(12) United States Patent
Asako

(10) Patent No.: US 8,192,967 B2
(45) Date of Patent: Jun. 5, 2012

(54) REDUCTASE, GENE THEREOF AND METHOD OF USING THE SAME

(75) Inventor: Hiroyuki Asako, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/532,099

(22) PCT Filed: Mar. 24, 2008

(86) PCT No.: PCT/JP2008/056257
§ 371 (c)(1),
(2), (4) Date: Sep. 18, 2009

(87) PCT Pub. No.: WO2008/114891
PCT Pub. Date: Sep. 25, 2008

(65) Prior Publication Data
US 2010/0112701 A1     May 6, 2010

(30) Foreign Application Priority Data

Mar. 22, 2007  (JP) ................. 2007-074377
Jan. 22, 2008  (JP) ................. 2008-011298

(51) Int. Cl.
| | |
|---|---|
| C12P 7/02 | (2006.01) |
| C12N 1/20 | (2006.01) |
| C12N 15/00 | (2006.01) |
| C07H 21/04 | (2006.01) |

(52) U.S. Cl. ............... 435/155; 435/252.3; 435/252.33; 435/320.1; 536/23.2

(58) Field of Classification Search .................. None
See application file for complete search history.

(56) References Cited

U.S. PATENT DOCUMENTS 5,194,380 A   3/1993  Matsuyama et al.
5,948,819 A   9/1999  Ohtsuka et al.

FOREIGN PATENT DOCUMENTS

WO      WO 0210101      2/2002

OTHER PUBLICATIONS da Silva et al. UniPort Accession No. Q8PDR4, May 29, 2007.*
Database: GenBank, Accession No. AE012123, May 23, 2002.*
Database: UniPort, Accession No. Q8PDR4, Nov. 28, 2006.*
daSilva et al. Comparison of the genomes of two Xanthomonas pathogens with different host specificities. Nature vol. 417, May 23, 2002, 459-463.*
Asako et al., "Penicillium citrinum Yurai no beta-keto ester kangen koso idenshi no daichokin deno hatsugen to fusai kangen han'no eno Tekiyo", Japan Society for Bioscience, Biotechnology, and Agrochemistry Taikai Koen Yoshishu, p. 180, Abstract No. 3A11A01 (2003).
Communication for EP Application No. 08739374.0 (PCT/JP2008/056257) dated Mar. 31, 2010, along with Supplementary European Search Report for EP Application No. 08739374 dated Mar. 23, 2010.
Ema et al., "Highly enantioselective and efficient synthesis of methyl (R)-o-chloromandelate with recombinant E. coli: toward practical and green access to clopidogrel", Communication, Organic & Biomolecular Chemistry, 5:1175-1176 (2007).
International Preliminary Report on Patentability for PCT/JP2008/056257 dated Sep. 22, 2009.
International Search Report for PCT/JP2008/056257 dated Apr. 22, 2008.
Ito et al., "Penicillium citrinum Yurai no beta-keto ester kangen koso to hokoso saiseikei koso no kyohatsugenkei ni yoru kogaku kassei alcohol no seisan", Japan Society for Bioscience, Biotechnology, and Agrochemistry Taikai Koen Yoshishu, p. 198, Abstract No. 3-5FP24 (2002).
Qian et al., "Comparative and functional genomic analyses of the pathogenicity of phytopathogen *Xanthomonas campestris* pv. *campestris*", Genome Research, 15:757-767 (2005).
Sun et al, "Ru-Catalyzed Asymmetric Hydrogenation of alpha-Ketoesters with CeCl3.7H2O as Additive", Organic Letters, 7(24):5425-5427 (2005).
Taylor et al., "An Oxidoreductase is Involved in Cercosporin Degradation by the Bacterium *Xanthomonas campestris* pv. *zinniae*", Applied and Environmental Microbiology, 72(9):6070-6078 (2006).
Yamazaki et al., "Stereoselectivity in the Microbial Reduction of (Trifluroacetyl)ferrocene and 2-Fluoroacetophenones", Tetrahedron: Asymmetry, 4(6):1287-1294 (1993).
Asako et al., "Penicillium citrinum Yurai no beta-keto ester kangen koso idenshi no daichokin deno hatsugen to fusai kangen han'no eno Tekiyo", Japan Society for Bioscience, Biotechnology, and Agrochemistry Taikai Koen Yoshishu, p. 180, Abstract No. 3A11A01 (2003)—English Translation.
Ito et al., "Penicillium citrinum Yurai no beta-keto ester kangen koso to hokoso saiseikei koso no kyohatsugenkei ni yoru kogaku kassei alcohol no seisan", Japan Society for Bioscience, Biotechnology, and Agrochemistry Taikai Koen Yoshishu, p. 198, Abstract No. 3-5FP24 (2002)—English Translation.

* cited by examiner

*Primary Examiner* — Nashaat Nashed
(74) *Attorney, Agent, or Firm* — Sughrue Mion, PLLC

(57) ABSTRACT

The present invention relates to a protein which can asymmetrically reduce an ortho-substituted phenylglyoxalic acid compound to produce an amide or ester compound of corresponding optically-active ortho-substituted mandelic acid compound with a good optical yield, a DNA encoding the protein, a process for producing the protein from the DNA, and a process for asymmetrically reducing an ortho-substituted phenylglyoxalic acid compound to produce a corresponding optically-active ortho-substituted mandelic acid compound.

19 Claims, No Drawings

SEQUENCE LISTING

<160> NUMBER OF SEQ ID NOS: 15

<210> SEQ ID NO 1
<211> LENGTH: 322
<212> TYPE: PRT
<213> ORGANISM: Xanthomonas campestris

<400> SEQUENCE: 1

Met Pro His Ser Arg Ala Leu Gly Arg Ser Gly Leu Gln Val Gln Pro
1               5                   10                  15

Ile Val Phe Gly Gly Asn Val Phe Gly Trp Ser Ala Asp Glu Ala Thr
            20                  25                  30

Ser Phe Ala Leu Leu Asp Ala Phe Val Asp Ala Gly Phe Asn Met Ile
        35                  40                  45

Asp Thr Ala Asp Ala Tyr Ser Ser Trp Val Pro Gly Asn Arg Gly Gly
    50                  55                  60

Glu Ser Glu Thr Ile Ile Gly Arg Trp Leu Ala Arg Ser Gly Lys Arg
65                  70                  75                  80

Asn Lys Val Leu Ile Ala Thr Lys Val Ala Lys Trp Ser Glu His Pro
                85                  90                  95

Gly Leu Ser Pro Asp Asn Ile Ala Ala Val Asp Asp Ser Leu Ser
            100                 105                 110

Arg Leu Gln Thr Asp Val Ile Asp Leu Tyr Gln Ala His Glu Asp Asp
        115                 120                 125

Glu Ser Ile Pro Leu Glu Ala Thr Leu Ala Ala Phe Gly Arg Leu Ile
    130                 135                 140

Glu Gln Gly Lys Val Arg Ala Ile Gly Ala Ser Asn Tyr Thr Ala Ala
145                 150                 155                 160

Arg Leu Arg Asp Ala Leu Asp Val Ser Ala Gln Tyr Asn Leu Pro Arg
                165                 170                 175

Tyr Glu Ser Leu Gln Pro Glu Tyr Asn Leu Tyr Asp Arg Ala Gly Phe
            180                 185                 190

Glu Asp Glu Leu Glu Pro Leu Val Gln Glu Arg Gly Leu Gly Val Ile
        195                 200                 205

Ser Tyr Tyr Ser Leu Ala Ser Gly Phe Leu Thr Gly Lys Tyr Arg Ser
    210                 215                 220

Ala Asn Asp Ala Gly Lys Ser Ser Ala Arg Gly Ala Ser Val Val Lys
225                 230                 235                 240

Gln Tyr Val Asn Pro Arg Gly Leu Arg Ile Leu Gln Ala Leu Asp Asp
                245                 250                 255

Leu Ala Thr His Thr Ala Thr Pro Ala Gln Ile Ala Leu Ala Trp
            260                 265                 270

Leu Ile Ala Arg Pro Ser Val Thr Ala Pro Ile Val Ser Ala Thr Ser
        275                 280                 285

Val Thr Gln Leu Gln Asp Val Leu Ala Ala Gly Gln Ile Thr Leu Ser
    290                 295                 300

Asp Ala Gln Ile Ala Gln Leu Asp Glu Ala Ser Ala Val Glu Pro Ala
305                 310                 315                 320

Gly Ala

<210> SEQ ID NO 2
<211> LENGTH: 969
<212> TYPE: DNA
<213> ORGANISM: Xanthomonas campestris
<220> FEATURE:

<221> NAME/KEY: CDS
<222> LOCATION: (1)..(966)

<400> SEQUENCE: 2

```
atg ccc cac tcc cgt gcg ctt ggc cgc tcc ggc ctg caa gtc cag ccg      48
Met Pro His Ser Arg Ala Leu Gly Arg Ser Gly Leu Gln Val Gln Pro
1               5                   10                  15 atc gtg ttc ggt ggc aac gtg ttt ggc tgg agc gcc gac gag gcc acc      96
Ile Val Phe Gly Gly Asn Val Phe Gly Trp Ser Ala Asp Glu Ala Thr
            20                  25                  30 tcg ttc gcg ttg ctc gac gcc ttc gtc gat gcc ggc ttc aac atg atc     144
Ser Phe Ala Leu Leu Asp Ala Phe Val Asp Ala Gly Phe Asn Met Ile
        35                  40                  45 gat acc gcc gac gcg tac tcc agt tgg gtg ccc ggc aat cgc ggt ggc     192
Asp Thr Ala Asp Ala Tyr Ser Ser Trp Val Pro Gly Asn Arg Gly Gly
    50                  55                  60 gaa tcg gaa acc atc atc ggc cgc tgg ctg gcc cgc agc ggc aaa cgc     240
Glu Ser Glu Thr Ile Ile Gly Arg Trp Leu Ala Arg Ser Gly Lys Arg
65                  70                  75                  80 aac aag gtg ctg atc gcc acc aag gtc gcc aag tgg agc gaa cac ccg     288
Asn Lys Val Leu Ile Ala Thr Lys Val Ala Lys Trp Ser Glu His Pro
                85                  90                  95 ggc ctg tcg ccg gac aac atc gca gcg gcg gtg gac gat tcg ctg tcg     336
Gly Leu Ser Pro Asp Asn Ile Ala Ala Ala Val Asp Asp Ser Leu Ser
            100                 105                 110 cgc ctg cag acc gat gtg atc gat ctg tac cag gca cac gaa gac gac     384
Arg Leu Gln Thr Asp Val Ile Asp Leu Tyr Gln Ala His Glu Asp Asp
        115                 120                 125 gaa tcg att ccg ctg gaa gcc acg ctg gcc gca ttc ggc cgg ctg atc     432
Glu Ser Ile Pro Leu Glu Ala Thr Leu Ala Ala Phe Gly Arg Leu Ile
    130                 135                 140 gaa cag ggc aag gtg cgt gcg atc ggc gcc tcc aac tac aca gcc gcg     480
Glu Gln Gly Lys Val Arg Ala Ile Gly Ala Ser Asn Tyr Thr Ala Ala
145                 150                 155                 160 cgc ctg cgc gat gcg ctg gat gtg tcg gcg caa tac aac ctg ccg cgc     528
Arg Leu Arg Asp Ala Leu Asp Val Ser Ala Gln Tyr Asn Leu Pro Arg
                165                 170                 175 tat gaa agc ctg cag ccc gaa tac aac ctc tac gac cgc gcc ggc ttc     576
Tyr Glu Ser Leu Gln Pro Glu Tyr Asn Leu Tyr Asp Arg Ala Gly Phe
            180                 185                 190 gaa gac gag ctg gaa ccg ctg gtg caa gaa cgc ggc ctg ggc gtg atc     624
Glu Asp Glu Leu Glu Pro Leu Val Gln Glu Arg Gly Leu Gly Val Ile
        195                 200                 205 agt tac tac tcg ctg gcc agc ggt ttt ctc acc ggc aag tac cgc agc     672
Ser Tyr Tyr Ser Leu Ala Ser Gly Phe Leu Thr Gly Lys Tyr Arg Ser
    210                 215                 220 gcc aat gac gcc ggc aag agc agc gcg cgt ggc gcc tcg gtg gtg aag     720
Ala Asn Asp Ala Gly Lys Ser Ser Ala Arg Gly Ala Ser Val Val Lys
225                 230                 235                 240 caa tac gtc aat ccg cgt ggc ttg cgc atc ctg cag gcg ctg gac gat     768
Gln Tyr Val Asn Pro Arg Gly Leu Arg Ile Leu Gln Ala Leu Asp Asp
                245                 250                 255 ctg gcc gcc acc cac acc gcc acg ccg gca cag att gcg ctg gcg tgg     816
Leu Ala Ala Thr His Thr Ala Thr Pro Ala Gln Ile Ala Leu Ala Trp
            260                 265                 270 ttg atc gcg cgc ccc agt gtc acc gcg ccg atc gtc agc gcc acc agc     864
Leu Ile Ala Arg Pro Ser Val Thr Ala Pro Ile Val Ser Ala Thr Ser
        275                 280                 285 gtg acc cag ttg cag gac gtg ctg gcg gcc ggg cag atc acg ctc agc     912
Val Thr Gln Leu Gln Asp Val Leu Ala Ala Gly Gln Ile Thr Leu Ser
    290                 295                 300
```

```
gat gcg cag atc gcg cag ctc gac gag gcc agc gca gtg gaa cca gcc      960
Asp Ala Gln Ile Ala Gln Leu Asp Glu Ala Ser Ala Val Glu Pro Ala
305                 310                 315                 320 ggc gcc tga                                                          969
Gly Ala <210> SEQ ID NO 3
<211> LENGTH: 969
<212> TYPE: DNA
<213> ORGANISM: Xanthomonas campestris
<220> FEATURE:
<221> NAME/KEY: CDS
<222> LOCATION: (1)..(966)

<400> SEQUENCE: 3 atg ccc cac tcc cgt gcg ctt ggc cgc tcc ggc ctg caa gtc cag ccg       48
Met Pro His Ser Arg Ala Leu Gly Arg Ser Gly Leu Gln Val Gln Pro
1               5                   10                  15

-continued

```
                Gln Tyr Val Asn Pro Arg Gly Leu Arg Ile Leu Gln Ala Leu Asp Asp
                                245                 250                 255 ctg gcc gcc acc cac acc gcc acg cct gca cag att gcg ctg gcg tgg       816
Leu Ala Ala Thr His Thr Ala Thr Pro Ala Gln Ile Ala Leu Ala Trp
            260                 265                 270 ttg atc gcg cgc ccc agt gtc acc gcg ccg atc gtc agc gcc acc agc       864
Leu Ile Ala Arg Pro Ser Val Thr Ala Pro Ile Val Ser Ala Thr Ser
        275                 280                 285 gtg acc cag ttg cag gac gtg ctg gcg gcc ggg cag atc acg ctc agc       912
Val Thr Gln Leu Gln Asp Val Leu Ala Ala Gly Gln Ile Thr Leu Ser
    290                 295                 300 gat gcg cag atc gcg cag ctc gac gag gcc agc gca gcg gaa cca gcc       960
Asp Ala Gln Ile Ala Gln Leu Asp Glu Ala Ser Ala Ala Glu Pro Ala
305                 310                 315                 320 ggc gcc tga                                                           969
Gly Ala <210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgccccact cccgtgcgct tggccgctcc                                      30

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcaggcgccg gctggttccg ctgcgctgg                                       29

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccatggcta tgccccactc ccgt                                            24

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctctagagtg tcaggcgccg gctggt                                          26

<210> SEQ ID NO 8
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 8
gatcatcata gcaggagtca t                                                21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaattcaaca ccagtcagct c                                                21

<210> SEQ ID NO 10
<211> LENGTH: 786
<212> TYPE: DNA
<213> ORGANISM: Bacillus megaterium
<220> FEATURE:
<221> NAME/KEY: CDS
<222> LOCATION: (1)..(783)

<400> SEQUENCE: 10

| atg | tat | aaa | gat | tta | gaa | gga | aaa | gta | gtt | gtc | ata | aca | ggt | tca | tct | 48 |
|-----|-----|-----|-----|-----|-----|-----|-----|-----|-----|-----|-----|-----|-----|-----|-----|----|
| Met | Tyr | Lys | Asp | Leu | Glu | Gly | Lys | Val | Val | Val | Ile | Thr | Gly | Ser | Ser |    |
| 1   |     |     |     | 5   |     |     |     |     | 10  |     |     |     |     | 15  |     |    |

| acc | ggt | tta | gga | aaa | gca | atg | gcg | att | cgt | ttt | gcg | aca | gaa | aaa | gct | 96 |
|-----|-----|-----|-----|-----|-----|-----|-----|-----|-----|-----|-----|-----|-----|-----|-----|----|
| Thr | Gly | Leu | Gly | Lys | Ala | Met | Ala | Ile | Arg | Phe | Ala | Thr | Glu | Lys | Ala |    |
|     |     |     | 20  |     |     |     |     | 25  |     |     |     |     | 30  |     |     |    |

| aaa | gta | gtt | gtg | aac | tat | cgt | tcg | aaa | gaa | gaa | gaa | gct | aac | agc | gtt | 144 |
|-----|-----|-----|-----|-----|-----|-----|-----|-----|-----|-----|-----|-----|-----|-----|-----|-----|
| Lys | Val | Val | Val | Asn | Tyr | Arg | Ser | Lys | Glu | Glu | Glu | Ala | Asn | Ser | Val |     |
|     |     | 35  |     |     |     |     | 40  |     |     |     |     | 45  |     |     |     |     |

| tta | gaa | gaa | att | aaa | aaa | gtg | ggc | gga | gag | gct | att | gcc | gtc | aaa | ggt | 192 |
|-----|-----|-----|-----|-----|-----|-----|-----|-----|-----|-----|-----|-----|-----|-----|-----|-----|
| Leu | Glu | Glu | Ile | Lys | Lys | Val | Gly | Gly | Glu | Ala | Ile | Ala | Val | Lys | Gly |     |
| 50  |     |     |     |     | 55  |     |     |     |     | 60  |     |     |     |     |     |     |

| gat | gta | aca | gtt | gag | tct | gat | gtg | atc | aat | tta | gtt | caa | tct | gct | att | 240 |
|-----|-----|-----|-----|-----|-----|-----|-----|-----|-----|-----|-----|-----|-----|-----|-----|-----|
| Asp | Val | Thr | Val | Glu | Ser | Asp | Val | Ile | Asn | Leu | Val | Gln | Ser | Ala | Ile |     |
| 65  |     |     |     |     | 70  |     |     |     |     | 75  |     |     |     |     | 80  |     |

| aaa | gaa | ttt | gga | aag | cta | gac | gtt | atg | att | aat | aac | gca | gga | atg | gaa | 288 |
|-----|-----|-----|-----|-----|-----|-----|-----|-----|-----|-----|-----|-----|-----|-----|-----|-----|
| Lys | Glu | Phe | Gly | Lys | Leu | Asp | Val | Met | Ile | Asn | Asn | Ala | Gly | Met | Glu |     |
|     |     |     |     | 85  |     |     |     |     | 90  |     |     |     |     | 95  |     |     |

| aat | ccg | gtt | tcg | tct | cat | gaa | atg | tct | tta | agt | gat | tgg | aat | aaa | gtc | 336 |
|-----|-----|-----|-----|-----|-----|-----|-----|-----|-----|-----|-----|-----|-----|-----|-----|-----|
| Asn | Pro | Val | Ser | Ser | His | Glu | Met | Ser | Leu | Ser | Asp | Trp | Asn | Lys | Val |     |
|     |     |     | 100 |     |     |     |     | 105 |     |     |     |     | 110 |     |     |     |

| att | gat | acg | aac | tta | acg | gga | gca | ttt | tta | ggc | agc | cgt | gaa | gcg | att | 384 |
|-----|-----|-----|-----|-----|-----|-----|-----|-----|-----|-----|-----|-----|-----|-----|-----|-----|
| Ile | Asp | Thr | Asn | Leu | Thr | Gly | Ala | Phe | Leu | Gly | Ser | Arg | Glu | Ala | Ile |     |
|     |     | 115 |     |     |     |     | 120 |     |     |     |     | 125 |     |     |     |     |

| aaa | tat | ttt | gtg | gaa | aat | gat | att | aag | gga | aca | gtt | att | aac | atg | tcg | 432 |
|-----|-----|-----|-----|-----|-----|-----|-----|-----|-----|-----|-----|-----|-----|-----|-----|-----|
| Lys | Tyr | Phe | Val | Glu | Asn | Asp | Ile | Lys | Gly | Thr | Val | Ile | Asn | Met | Ser |     |
| 130 |     |     |     |     | 135 |     |     |     |     | 140 |     |     |     |     |     |     |

| agt | gtt | cac | gag | aaa | att | cct | tgg | cca | tta | ttt | gtt | cat | tac | gca | gca | 480 |
|-----|-----|-----|-----|-----|-----|-----|-----|-----|-----|-----|-----|-----|-----|-----|-----|-----|
| Ser | Val | His | Glu | Lys | Ile | Pro | Trp | Pro | Leu | Phe | Val | His | Tyr | Ala | Ala |     |
| 145 |     |     |     |     | 150 |     |     |     |     | 155 |     |     |     |     | 160 |     |

| agt | aaa | ggc | gga | atg | aag | ctc | atg | acc | gaa | aca | ctt | gca | tta | gaa | tac | 528 |
|-----|-----|-----|-----|-----|-----|-----|-----|-----|-----|-----|-----|-----|-----|-----|-----|-----|
| Ser | Lys | Gly | Gly | Met | Lys | Leu | Met | Thr | Glu | Thr | Leu | Ala | Leu | Glu | Tyr |     |
|     |     |     |     | 165 |     |     |     |     | 170 |     |     |     |     | 175 |     |     |

| gct | cca | aaa | ggt | att | cgt | gta | aat | aac | att | gga | cca | gga | gcg | att | aat | 576 |
|-----|-----|-----|-----|-----|-----|-----|-----|-----|-----|-----|-----|-----|-----|-----|-----|-----|
| Ala | Pro | Lys | Gly | Ile | Arg | Val | Asn | Asn | Ile | Gly | Pro | Gly | Ala | Ile | Asn |     |
|     |     |     | 180 |     |     |     |     | 185 |     |     |     |     | 190 |     |     |     |

| aca | ccg | att | aac | gct | gag | aaa | ttt | gct | gat | cct | gag | cag | cgt | gca | gat | 624 |
|-----|-----|-----|-----|-----|-----|-----|-----|-----|-----|-----|-----|-----|-----|-----|-----|-----|

```
                        Thr Pro Ile Asn Ala Glu Lys Phe Ala Asp Pro Glu Gln Arg Ala Asp
                                        195                 200                 205 gta gaa agc atg att cca atg gga tac att gga gag ccg gaa gaa att       672
Val Glu Ser Met Ile Pro Met Gly Tyr Ile Gly Glu Pro Glu Glu Ile
        210                 215                 220 gca gcg gtt gct gca tgg cta gct tct tca gag gca agt tat gta aca       720
Ala Ala Val Ala Ala Trp Leu Ala Ser Ser Glu Ala Ser Tyr Val Thr
225                 230                 235                 240 ggg att aca ctc ttt gct gac ggc ggt atg aca cag tac cca tca ttc       768
Gly Ile Thr Leu Phe Ala Asp Gly Gly Met Thr Gln Tyr Pro Ser Phe
            245                 250                 255 caa gca gga cgc gga taa                                               786
Gln Ala Gly Arg Gly
                260

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccatggcta tgtataaaga tttagaa                                          27

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cggatccgtt atccgcgtcc tgc                                              23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggatccgag gaaacagacc atgg                                             24

<210> SEQ ID NO 14
<211> LENGTH: 322
<212> TYPE: PRT
<213> ORGANISM: Xanthomonas campestris

<400> SEQUENCE: 14

Met Pro His Ser Arg Ala Leu Gly Arg Ser Gly Leu Gln Val Gln Pro
1               5                   10                  15

Ile Val Phe Gly Gly Asn Val Phe Gly Trp Ser Ala Asp Glu Ala Thr
                20                  25                  30

Ser Phe Ala Leu Leu Asp Ala Phe Val Asp Ala Gly Phe Asn Met Ile
            35                  40                  45

Asp Thr Ala Asp Ala Tyr Ser Gly Trp Val Pro Gly Asn Arg Gly Gly
        50                  55                  60

Glu Ser Glu Thr Ile Ile Gly Arg Trp Leu Ala Arg Ser Gly Lys Arg
65                  70                  75                  80
```

```
Asp Lys Val Leu Ile Ala Thr Lys Val Ala Lys Trp Ser Glu His Pro
                85                  90                  95
Gly Leu Ser Pro Asp Asn Ile Ala Ala Val Glu Asp Ser Leu Ser
            100                 105                 110
Arg Leu Gln Thr Asp Val Ile Asp Leu Tyr Gln Ala His Glu Asp Asp
            115                 120                 125
Glu Ser Ile Pro Leu Glu Ala Thr Leu Ala Ala Phe Gly Arg Leu Ile
130                 135                 140
Glu Gln Gly Lys Val Arg Ala Ile Gly Ala Ser Asn Tyr Thr Ala Ala
145                 150                 155                 160
Arg Leu Arg Asp Ala Leu Asp Val Ser Ala Gln Tyr Asn Leu Pro Arg
                165                 170                 175
Tyr Glu Ser Leu Gln Pro Glu Tyr Asn Leu Tyr Asp Arg Ala Gly Phe
            180                 185                 190
Glu Glu Glu Leu Glu Pro Leu Val Gln Glu Arg Gly Leu Gly Val Ile
            195                 200                 205
Ser Tyr Tyr Ser Leu Ala Ser Gly Phe Leu Thr Gly Lys Tyr Arg Ser
210                 215                 220
Ala Asp Asp Ala Gly Lys Ser Ser Ala Arg Gly Ala Ser Val Val Lys
225                 230                 235                 240
Gln Tyr Val Asn Pro Arg Gly Leu Arg Ile Leu Gln Ala Leu Asp Asp
                245                 250                 255
Leu Ala Ala Thr His Thr Ala Thr Pro Ala Gln Ile Ala Leu Ala Trp
            260                 265                 270
Leu Ile Ala Arg Pro Ser Val Thr Ala Pro Ile Val Ser Ala Thr Ser
            275                 280                 285
Val Thr Gln Leu Gln Asp Val Leu Ala Ala Gly Gln Ile Thr Leu Ser
            290                 295                 300
Asp Ala Gln Ile Ala Gln Leu Asp Glu Ala Ser Ala Ala Glu Pro Ala
305                 310                 315                 320
Gly Ala

<210> SEQ ID NO 15
<211> LENGTH: 261
<212> TYPE: PRT
<213> ORGANISM: Bacillus megaterium

<400> SEQUENCE: 15

Met Tyr Lys Asp Leu Glu Gly Lys Val Val Ile Thr Gly Ser Ser
1               5                   10                  15
Thr Gly Leu Gly Lys Ala Met Ala Ile Arg Phe Ala Thr Glu Lys Ala
            20                  25                  30
Lys Val Val Val Asn Tyr Arg Ser Lys Glu Glu Ala Asn Ser Val
            35                  40                  45
Leu Glu Glu Ile Lys Lys Val Gly Gly Glu Ala Ile Ala Val Lys Gly
        50                  55                  60
Asp Val Thr Val Glu Ser Asp Val Ile Asn Leu Val Gln Ser Ala Ile
65                  70                  75                  80
Lys Glu Phe Gly Lys Leu Asp Val Met Ile Asn Asn Ala Gly Met Glu
                85                  90                  95
Asn Pro Val Ser Ser His Glu Met Ser Leu Ser Asp Trp Asn Lys Val
            100                 105                 110
Ile Asp Thr Asn Leu Thr Gly Ala Phe Leu Gly Ser Arg Glu Ala Ile
            115                 120                 125
```

-continued

```
Lys Tyr Phe Val Glu Asn Asp Ile Lys Gly Thr Val Ile Asn Met Ser
    130             135             140

Ser Val His Glu Lys Ile Pro Trp Pro Leu Phe Val His Tyr Ala Ala
145             150             155             160

Ser Lys Gly Gly Met Lys Leu Met Thr Glu Thr Leu Ala Leu Glu Tyr
            165             170             175

Ala Pro Lys Gly Ile Arg Val Asn Asn Ile Gly Pro Gly Ala Ile Asn
            180             185             190

Thr Pro Ile Asn Ala Glu Lys Phe Ala Asp Pro Glu Gln Arg Ala Asp
        195             200             205

Val Glu Ser Met Ile Pro Met Gly Tyr Ile Gly Glu Pro Glu Glu Ile
    210             215             220

Ala Ala Val Ala Ala Trp Leu Ala Ser Ser Glu Ala Ser Tyr Val Thr
225             230             235             240

Gly Ile Thr Leu Phe Ala Asp Gly Gly Met Thr Gln Tyr Pro Ser Phe
            245             250             255

Gln Ala Gly Arg Gly
            260
```

REDUCTASE, GENE THEREOF AND METHOD OF USING THE SAME

SEQUENCE LISTING

The instant application contains a Sequence Listing which has been submitted via EFS-Web and is hereby incorporated by reference in its entirety. Said ASCII copy, created on Oct. 16, 2009, is named Q115177.txt, and is 21,414 bytes in size.

TECHNICAL FIELD

The present invention relates to a novel reductase and a DNA encoding the same, a recombinant vector containing the DNA, and a transformant transformed with the recombinant vector. The present invention also relates to a process for producing an optically-active mandelic acid compound which is an optically active alcohol, using the novel reductase or the transformant.

BACKGROUND ART

Optically-active ortho-substituted mandelic acid compounds are compounds useful in production of medicines, agricultural chemicals and so on, and production processes using asymmetric reducing reagents or the like have been proposed, but in the process described in International Publication No. WO 0210101, further recrystallization or the like is performed after a reaction in order to increase an optical purity and, also in a reaction described in Organic Letters, 2005, vol. 7, No. 24, 5425-5427, it cannot be necessarily said that an optical yield of the reaction is sufficient, In addition, has not been known a method of asymmetrically reducing a keto group of a phenylglyoxylic acid compound, the group having a substituent at an ortho-position and being in the sterically-complicated environment, to an optically-active mandelic acid compound using a microorganism or the like.

DISCLOSURE OF THE INVENTION

The present invention provides a method of reducing a phenylglyoxalic acid compound having a substituent at an ortho-position to an optically active mandelic acid compound with a good optical yield.

More specifically, the present invention provides a protein which can asymmetrically reduce an ortho-substituted phenylglyoxalic acid compound to produce an optically-active ortho-substituted mandelic acid compound with a good optical yield, a DNA encoding the protein (hereinafter, abbreviated as invented DNA), a transformant comprising the DNA, a process for producing the protein from the DNA, and a process for asymmetrically reducing an ortho-substituted phenylglyoxalic acid compound to produce a corresponding optically-active ortho-substituted mandelic acid compound.

That is, the present invention provides:

1. A DNA comprising any of the following nucleotide sequence:
   a) a nucleotide sequence encoding the amino acid sequence of SEQ ID NO:1; and
   b) the nucleotide sequence of SEQ ID NO:2;

2. A DNA in which a promoter functional in a host cell and a DNA comprising any nucleotide sequence of the following a) to d) are operably linked:
   a) a nucleotide sequence encoding the amino acid sequence of SEQ ID NO:1;
   b) a nucleotide sequence of a DNA, wherein the DNA has at least 90% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically active ortho-substituted mandelic acid;
   c) a nucleotide sequence of a DNA, wherein the DNA hybridizes under a stringent condition with a DNA comprising a nucleotide sequence encoding the amino acid sequence of SEQ ID NO: 1, and wherein the nucleotide sequence encodes an amino acid sequence of a protein having the ability to asymmetrically reduce an ortho-substituted phenylglyoxalic acid compound to produce corresponding optically-active ortho-substituted mandelic acid compound; and
   d) the nucleotide sequence of SEQ ID NO:2;

3. A recombinant vector comprising the DNA according to the item 1 or 2;

4. A transformant in which the DNA of the item 2 or the recombinant vector of the item 3 has been introduced into a host cell;

5. The transformant according to the item 4, wherein the host cell is a microorganism;

6. The transformant according to the item 4, wherein the host cell is *Escherichia coli*;

7. A transformant comprising a DNA comprising any of the following nucleotide sequence:
   a) a nucleotide sequence encoding the amino acid sequence of SEQ ID NO:1;
   b) a nucleotide sequence of a DNA, wherein the DNA has at least 90% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically active ortho-substituted mandelic acid compound;
   c) a nucleotide sequence of a DNA, wherein the DNA hybridizes under a stringent condition with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid compound to produce corresponding optically-active ortho-substituted mandelic acid compound; and
   d) the nucleotide sequence of SEQ ID NO:2;

8. A process for producing a transformant comprising a step of introducing the recombinant vector of the item 3 into a host cell;

9. A protein comprising any of the following amino acid sequence;
   a) the amino acid sequence of SEQ ID NO:1; and
   b) an amino acid sequence in which one or a plurality of amino acids are deleted, substituted or added in the amino acid sequence of SEQ ID NO:1, and which is an amino acid sequence of a protein having the ability to asymmetrically reduce an ortho-substituted phenylglyoxalic acid compound to produce a corresponding optically-active ortho-substituted mandelic acid compound;

10. A recombinant vector comprising i) a DNA comprising any nucleotide sequence of the following a) to d) and ii) a DNA comprising a nucleotide sequence encoding an amino acid sequence of a protein having the ability to convert oxidized β-nicotineamide adenine dinucleotide or oxidized β-nicotineamide adenine dinucleotide phosphate into a reduced form:
   a) a nucleotide sequence encoding the amino acid sequence of SEQ ID NO:1;

b) a nucleotide sequence of a DNA, wherein the DNA has at least 90% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically active ortho-substituted mandelic acid compound;

c) a nucleotide sequence of a DNA, wherein the DNA hybridizes under a stringent condition with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid compound to produce corresponding optically-active ortho-substituted mandelic acid compound; and d) the nucleotide sequence of SEQ ID NO:2;

11. The recombinant vector according to the item 10, wherein the protein having the ability to convert oxidized β-nicotineamide adenine dinucleotide or oxidized R-nicotineamide adenine dinucleotide phosphate into a reduced form is glucose dehydrogenase;

12. The recombinant vector according to the item 11, wherein the protein having glucose dehydrogenase activity is glucose dehydrogenase derived from *Bacillus megaterium;*

13. A transformant, in which any of recombinant vector of the items 10 to 12 has been introduced into a host cell;

14. The transformant according to the item 13, wherein the host cell is a microorganism;

15. The transformant according to the item 13, wherein the host cell is *Escherichia coli;*

16. A transformant comprising a DNA comprising any nucleotide sequence of the following a) to d) and a DNA comprising a nucleotide sequence encoding an amino acid sequence of a protein having the ability to convert oxidized R-nicotineamide adenine dinucleotide or oxidized β-nicotineamide adenine dinucleotide phosphate into a reduced form:

a) a nucleotide sequence encoding the amino acid sequence of SEQ ID NO:1;

b) a nucleotide sequence of a DNA, wherein the DNA has at least 90% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically active ortho-substituted mandelic acid compound;

c) a nucleotide sequence of a DNA, wherein the DNA hybridizes under a stringent condition with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid compound to produce corresponding optically-active ortho-substituted mandelic acid compound; and d) the nucleotide sequence of SEQ ID NO:2;

17. A process for producing an optically-active alcohol compound comprising reacting the protein of the item 9, or the transformant of any of the items 4 to 7, and 13 to 16, or a treated product thereof with a prochiral carbonyl compound;

18. A process for producing an optically-active ortho-substituted mandelic acid compound represented by the formula (2):

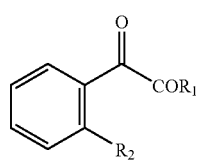

(2)

(wherein $R_1$ and $R_2$ are as defined above, and a carbon atom with a * symbol is an asymmetric carbon atom)

comprising bringing an ortho-substituted phenylglyoxalic acid compound represented by the formula (1):

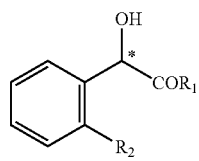

(1)

(wherein $R_1$ represents an optionally substituted amino group, or an optionally substituted alkoxy group, and $R_2$ represents an optionally substituted C1-8 alkyl group)

into contact with a protein which comprises any amino acid sequence of the following a) to f) and which has an ability to asymmetrically reduce the compound of the formula (1) to optically-active compound of the formula (2);

a) the amino acid sequence of SEQ ID NO:1;

b) an amino acid sequence which is encoded by a nucleotide sequence having at least 90% DNA sequence homology with a DNA comprising the nucleotide sequence of SEQ ID NO:2;

c) an amino acid sequence which is encoded by a nucleotide sequence of a DNA which hybridizes under a stringent condition with a DNA comprising the nucleotide sequence of SEQ ID NO:2;

d) an amino acid sequence in which one or a plurality of amino acids are deleted, substituted or added in the amino acid sequence of SEQ ID NO:1;

e) an amino acid sequence which is encoded by a nucleotide sequence of a DNA which hybridizes under a stringent condition with a DNA comprising a nucleotide sequence encoding the amino acid sequence of SEQ ID NO:1; and f) an amino acid sequence in which one or a plurality of amino acids are deleted, substituted or added in the amino acid sequence of SEQ ID NO:1; and 19. The process according to the item 17, wherein the prochiral carbonyl compound is an ortho-substituted phenylglyoxalic acid compound represented by the formula (1):

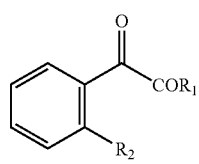

(1)

(wherein $R_1$ represents an optionally substituted amino group, or an optionally substituted alkoxy group, and $R_2$ represents an optionally substituted C1-8 alkyl group)

and the optically-active alcohol compound is an optically-active ortho-substituted mandelic acid compound represented by the formula (2):

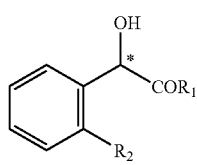

(2)

(wherein R₁ and R₂ are as defined above, and a carbon atom with a * symbol is an asymmetric carbon atom).

According to the present invention, useful optically-active ortho-substituted mandelic acid compounds such as (R)-2-(2-(2,5-dimethylphenoxymethyl)phenyl)-N-methyl-2-hydroxy-acetamide can be produced with a good optical yield.

BEST MODE FOR CARRYING OUT THE INVENTION

First, the invented DNA will be described. The invented DNA may be a natural DNA, or a DNA produced by introducing mutation (site-directed mutagenesis, mutation treatment etc.) into a natural DNA. When the natural DNA is retrieved, a subject may be a microorganism having the ability to asymmetrically reduce an ortho-substituted phenylglyoxalic acid compound, for example, an amide or ester compound of an ortho-substituted phenylglyoxalic acid compound to a corresponding optically active ortho-substituted mandelic acid compound, specifically, an amide or ester compound of optically active ortho-substituted mandelic acid, more particularly, for example, a microorganism having the ability to asymmetrically reduce 2-(2-(2,5-dimethylphenoxymethyl)phenyl)-N-methyl-2-oxo-acetamide to produce (R)-2-(2-(2,5-dimethylphenoxymethyl)phenyl)-N-methyl-2-hydroxy-acetamide. The invented DNA can be obtained from, for example, a microorganism belonging to genus Xanthomonas such as Xanthomonas campestris IFO13551 strain. The invented DNA may be such a natural DNA, or a DNA produced by introducing mutation into such a natural DNA by a method described later (site-directed mutagenesis, mutation treatment etc.).

The "DNA which hybridizes under a stringent condition with a DNA comprising a nucleotide sequence encoding the amino acid sequence of SEQ ID NO:1" in the invented DNA refers to a DNA such that, in Southern hybridization method described, for example, in "Cloning and Sequence" (supervised by Itaru Watanabe, edited by Masahiro Sugiura, 1989, published by Nouson Bunkasha), (1) it forms a DNA-DNA hybrid with a DNA comprising a nucleotide sequence encoding the amino acid sequence of SEQ ID NO:1 by hybridization at 65° C. under a high ion concentration [for example, 6×SSC (900 mM sodium chloride, 90 mM sodium citrate)], and (2) the hybrid is retained even after incubation at 65° C. for 30 minutes under a low ion concentration [for example, 0.1×SSC (15 mM sodium chloride, 1.5 mM sodium citrate)].

Specifically, examples include a DNA comprising a nucleotide sequence encoding the amino acid sequence of SEQ ID NO:1, a DNA comprising a nucleotide sequence in which, in a nucleotide sequence encoding the amino acid sequence of SEQ ID No: 1, apart of nucleotides are deleted, substituted or added, a DNA having at least 90% sequence homology, preferably at least 95% sequence homology, more preferably at least 99% sequence homology with a DNA comprising a nucleotide sequence encoding the amino acid sequence of SEQ ID No: 1, and the like.

The DNA may be a DNA cloned from naturally occurring DNAs, a DNA in which, in a nucleotide sequence of this cloned DNA, deletion, substitution or addition of a part of nucleotides is artificially introduced, or an artificially synthesized DNA. The sequence homology can be calculated using a tool for sequence analysis such as BESTFIT program supplied by UWGCG Package (Devereux et al (1984) Nucleic Acids Research 12, p 387-395), and PILEUP and BLAST algorism (Altschul S. F. (1993) J Mol Evol 36:290-300; Altschul S. F. (1990) J Mol Biol 215:403-10).

The invented DNA can be prepared, for example, as follows.

The invented DNA can be prepared by amplifying a DNA comprising a nucleotide sequence encoding the amino acid sequence of SEQ ID NO:1, a DNA comprising a nucleotide sequence encoding an amino acid sequence in which one or a plurality of amino acids are deleted, substituted or added in the amino acid sequence of SEQ ID NO:1 and/or a DNA comprising the nucleotide sequence of SEQ ID NO:2, by preparing a DNA library from a microorganism belonging to genus Xanthomonas such as Xanthomonas campestris according to conventional genetic engineering procedures (e.g. method described in "New Cellular Technology Experimental Protocol" (edited by the Institute of Medical Science, the University of Tokyo, Anticancer Research Section, Shujunsha, 1993)), and performing PCR employing the prepared DNA library as a template, and using appropriate primers.

In addition, the invented DNA can be prepared by amplifying a DNA comprising the nucleotide sequence of SEQ ID NO:2 by performing PCR employing the DNA library as a template, and using an oligonucleotide comprising the nucleotide sequence of SEQ ID NO:6 and an oligonucleotide comprising the nucleotide sequence of SEQ ID NO:7 as primers.

Examples of the condition of the PCR include the condition of heating a reaction solution obtained by mixing each 20 μM of four kinds of dNTPs, each 15 pmol of two kinds of oligonucleotide primers, 1.3 U of Taqpolymerase, and a DNA library as a template at 94° C. for 2 minutes, thereafter, performing 10 times of a cycle of 94° C. (10 seconds)-65° C. (30 seconds)-72° C. (90 seconds), then, times of a cycle of 94° C. (10 seconds)-65° C. (30 seconds)-72° C. (1 minute+5 seconds/cycle), and further retaining the solution at 72° C. for 7 minutes.

In addition, a restriction enzyme recognition sequence or the like may be added to the 5' end and/or the 3' end of the primer used in the PCR.

In addition, also by performing PCR employing the DNA library as a template, and using an oligonucleotide comprising a partial nucleotide sequence selected from nucleotide sequences encoding the amino acid sequence of SEQ ID NO:1 (e.g. an oligonucleotide comprising a nucleotide sequence of about 14 or more nucleotides on the 5'-terminal side encoding the amino acid sequence of SEQ ID No:1) or the like and an oligonucleotide of about 14 or more nucleotides comprising a nucleotide sequence complementary to a nucleotide sequence adjacent to a DNA-insertion site of a vector used in construction of the DNA library as primers, a DNA comprising a nucleotide sequence encoding the amino acid sequence of SEQ ID NO:1, a DNA comprising a nucleotide sequence encoding an amino acid sequence in which one or a plurality of amino acids are deleted, substituted or added in the amino acid sequence of SEQ ID NO:1, or the like can be amplified to prepare the invented DNA.

The thus amplified DNA is cloned into a vector according to a method described in "Molecular Cloning: A Laboratory Manual 2$^{nd}$ edition" (1989), Cold Spring Harbor Laboratory Press, "Current Protocols in Molecular Biology" (1987), John Wiley & Sons, Inc. ISBNO-471-50338-X or the like, whereby the invented vector can be obtained. Specific examples of the vector used include pUC119 (manufactured by Takara Shuzou), pTV118N (manufactured by Takara Shuzou), pBluescriptll (manufactured by Toyobo), pCR2.1-TOPO (manufactured by Invitrogen), pTrc99A (manufactured byPharmacia), pKK223-3 (manufactured by Pharmacia) and the like.

In addition, the invented DNA can also be obtained, for example, by hybridizing, as a probe, a DNA comprising a nucleotide sequence of about 15 or more nucleotides having a partial nucleotide sequence selected from nucleotide sequences encoding the amino acid sequence of SEQ ID NO:1 to a DNA library inserted in a vector derived from a microorganism or a phage under the condition described later, and detecting a DNA to which the probe specifically binds.

Examples of a method of hybridizing a probe to a chromosomal DNA or a DNA library include colony hybridization and plaque hybridization, and the method can be selected depending on a kind of a vector used in preparing a library.

When the library used is prepared using a plasmid vector, colony hybridization may be utilized. Specifically, a transformant is obtained by introducing a DNA of a library into a host microorganism, the result transformant is diluted, and then the dilution is seeded on an agar medium, and this is cultured until a colony appears.

When the library used is prepared using a phage vector, plaque hybridization may be utilized. Specifically, a host microorganism and a phage of a library are mixed under the infectable condition, the mixture is further mixed with a soft agar medium, and then the mixture is seeded on an agar medium, and this is cultured until a plaque appears.

Then, in either hybridization, a membrane is placed on an agar medium on which the culturing has been performed, and a transformant or a phage is adsorbed or transferred on the membrane. This membrane is alkali-treated, and subjected to neutralization treatment and, then, a DNA is subjected to fixation on the membrane. More specifically, in the case of plaque hybridization, a nitrocellulose membrane or a nylon membrane (e.g. Hybond-N$^+$ (trade mark, Amersham)) is placed on the agar medium, and this is allowed to stand still for about minute to adsorb or transfer phage particles onto the membrane. Then, the membrane is immersed in an alkali solution (e.g. 1.5 M sodium chloride, 0.5 M sodium hydroxide) for about 3 minutes to lyse the phage particles, whereby a phage DNA is eluted on the membrane, and this is immersed in a neutralization solution (e.g. 1.5 M sodium chloride, 0.5 M Tris-hydrochloric acid buffer pH 7.5) for about 5 minutes. Then, the membrane is washed with a washing solution (e.g. 0.3 M sodium chloride, 30 mM citric acid, 0.2 M Tris-hydrochloric acid buffer pH 7.5) for about 5 minutes, thereafter, the phage DNA is fixed on the membrane, for example, by heating at about 80° C. for about 90 minutes.

The thus prepared membrane is used to perform hybridization using the DNA as a probe. Hybridization can be performed, for example, according to the description of J. Sambrook, E. F. Frisch, T. Maniatis "Molecular Cloning: A Laboratory Manual 2$^{nd}$ edition (1989)" Cold Spring Harbor Laboratory Press or the like.

The DNA used in the probe may be labeled with a radioactive isotope element, or may be labeled with a fluorescent dye.

Examples of a method of labeling the DNA used in the probe with a radioactive isotope element include a method of performing PCR using the DNA used in the probe as a template, by replacing dCTP in a PCR reaction solution with ($\alpha$-$^{32}$ P) dCTP utilizing, for example, Random Primer Labeling Kit (manufactured by Takara Shuzou).

In addition, when the DNA used in the probe is labeled with a fluorescent dye, for example, ECL Direct Nucleic Acid Labeling and Detection System manufactured by Amersham can be used.

Hybridization can be performed, for example, as follows.

A pre-hybridization solution containing 450 to 900 mM sodium chloride, 45 to 90 mM sodium citrate, sodium dodecylsulfate (SDS) at a concentration of 0.1 to 1.0% by weight, a denatured non-specific DNA at a concentration of 0 to 200 µl/ml, and optionally containing albumin, Ficoll, polyvinylpyrrolidone or the like at a concentration of 0 to 0.2% by weight, respectively (preferably, apre-hybridization solution containing 900 mM sodium chloride, 90 mM sodium citrate, 1.0% by weight of SDS and 100 µl/ml denatured Calf-thymus DNA) is prepared at a ratio of 50 to 200 µl per 1 cm$^2$ of the membrane prepared above, and the membrane is immersed in the pre-hybridized solution, and retained at 42 to 65° C. for 1 to 4 hours.

Then, for example, a solution obtained by mixing a hybridization solution containing 450 to 900 mM sodium chloride, 45 to 90 mM sodium citrate, SDS at a concentration of 0.1 to 1.0% by weight, a denatured non-specific DNA at a concentration of 0 to 200 µg/ml, and optionally containing albumin, Ficoll, polyvinylpyrrolidone or the like at a concentration of 0 to 0.2% by weight, respectively (preferably, a hybridization solution containing 900 mM sodium chloride, 90 mM sodium citrate, 1.0% by weight of SDS and 100 µg/ml denatured Calf-thymus DNA), and the probe prepared by the aforementioned method ($1.0 \times 10^4$ to $2.0 \times 10^6$ cpm equivalent amount per 1 cm$^2$ of the membrane) is prepared at a ratio of 50 to 200 µl per 1 cm$^2$ of the membrane, and the membrane is immersed in the hybridization solution, and retained at 42 to 65° C. for 12 to 20 hours.

After the hybridization, the membrane is removed, and washed using a washing solution containing 15 to 300 mM sodium chloride, 1.5 to 30 mM sodium citrate and 0.1 to 1.0% by weight of SDS at 42 to 65° C. (preferably, a washing solution containing 15 mM sodium chloride, 1.5 mM sodium citrate and 1.0% by weight of SDS at 65° C.) or the like. The washed membrane is mildly rinsed with 2×SSC (300 mM sodium chloride, 30 mM sodium citrate), and dried. This membrane is subjected to, for example, autoradiography, and a position of the probe on the membrane is detected, whereby a clone corresponding to a position on the membrane of a DNA which hybridizes with the probe used is specified on the original agar medium, and this is picked up, whereby a clone having the DNA is isolated.

From a cultured bacterial cell obtained by culturing the thus obtained clone, the invented DNA can be prepared.

The DNA prepared as described above is cloned into a vector according to a method described in "Molecular Cloning; A Laboratory Manual 2$^{nd}$ edition" (1989), Cold Spring Harbor Laboratory Press, "Current Protocols in Molecular Biology" (1987), John Wiley & Sons, Inc. ISBNO-471-50338-X or the like, whereby the invented recombinant vector can be obtained. Examples of the vector used include, pUC119 (manufactured by Takara Shuzou), pTV118N (manufactured by Takara Shuzou), pBluescriptII (manufactured by Toyobo), pCR2.1-TOPO (manufactured by Invitrogen), pTrc99A (manufactured by Pharmacia), pKK223-3 (manufactured by Pharmacia) and the like.

In addition, a nucleotide sequence of the DNA can be analyzed by a dideoxy terminator method described in F. Sanger, S. Nicklen, A. R. Coulson, Proceeding of Natural Academy of Science U.S.A. (1977) 74: 5463-5467, or the like. For preparing a sample for nucleotide sequence analysis, a commercially available reagent such as ABI PRISM Dye Terminator Cycle Sequencing Ready Reaction Kit of Perkin Elmer may be used.

Confirmation that the DNA obtained as described above encodes an amino acid sequence of a protein having the ability to asymmetrically reduce an ortho-substituted phenylglyoxalic acid compound, typically, an amide or ester compound thereof (e.g. 2-(2-(2,5-dimethylphenoxymethyl)phenyl)-N-methyl-2-oxo-acetamide) to an optically-active ortho-substituted mandelic acid compound, typically, an amide or ester compound thereof (e.g. (R)-2-(2-(2,5-dimethylphenoxymethyl)phenyl)-N-methyl-2-hydroxy-acetamide) can be performed, for example, as follows.

First, the DNA obtained as described above is inserted into a vector so that it can be linked to the downstream of a promoter functional in a host cell as described later, and this vector is introduced into a host cell to obtain a transformant. Then, a culture of the transformant is made to act on an ortho-substituted phenylglyoxalic acid compound (for example, 2-(2-(2,5-dimethylphenoxymethyl)phenyl)-N-methyl-2-oxo-acetamide). By analyzing an amount of a corresponding optically-active ortho-substituted mandelic acid compound (for example, (R)-2-(2-(2,5-dimethylphenoxymethyl)phenyl)-N-methyl-2-hydroxy-acetamide) in the reaction product, it can be confirmed that the resulting DNA encodes an amino acid sequence of a protein having such ability.

In order to express the invented DNA in a host cell, for example, a DNA in which a promoter functional in a host cell and the invented DNA are operably linked is introduced into a host cell.

Herein, the "operably" means that upon transformation of a host cell by introduction of the DNA into a host cell, the invented DNA is in the state where it is bound to a promoter so as to be expressed under control of the promoter. Examples of the promoter include a promoter of the lactose operon of *Escherichia coli*, a promoter of the tryptophan operon of *Escherichia coli*, and a synthetic promoter functional in *Escherichia coli* such as a tac promoter and a trc promoter, and a promoter which controls expression of the invented DNA in *Xanthomonas campestris* may be utilized.

Generally, a recombinant vector obtained by inserting a DNA operably linked to a promoter functional in a host cell into the aforementioned vector is introduced into a host cell. When a vector including a selection marker gene (e.g. an antibiotic resistance imparting gene such as a kanamycin resistant gene, a neomycin resistant gene etc.) is used as a vector, a transformant into which the vector is introduced can be selected using a phenotype of the selection marker gene or the like as an index.

Examples of the host cell into which the invented DNA operably linked to a promoter functional in a host cell, or the invented recombinant vector is introduced include a microorganism belonging to genus *Escherichia*, genus *Bacillus*, genus *Corynebacterium*, genus *Staphylococcus*, genus *Streptomyces*, genus *Saccharomyces*, genus *Kluyveromyces*, genus *Pichia*, genus *Rhodococcus* and genus *Aspergillus*.

A method of introducing the invented DNA operably linked to a promoter functional in a host cell, or the invented recombinant vector into a host cell may be a conventionally used introduction method depending on a host cell used, and examples include a calcium chloride method described in "Molecular Cloning: A Laboratory Manual $2^{nd}$ edition" (1989), Cold Spring Harbor Laboratory Press, "Current Protocols in Molecular Biology" (1987), John Wiley & Sons, Inc. ISBN0-471-50338-X or the like, and an electroporation method described in "Methods in Electroporation: Gene Pulser/*E. coli* Pulser System" Bio-Rad Laboratories, (1993) or the like.

In order to select a transformant into which the invented DNA operably linked to a promoter functional in a host cell, or the invented recombinant vector has been introduced, for example, the transformant may be selected using, as an index, a phenotype of a selection marker gene contained in the vector.

Confirmation that the transformant harbors the invented DNA can be performed by confirmation of a restriction enzyme site, analysis of a nucleotide sequence, Southern hybridization, Western hybridization or the like according to conventional methods described in "Molecular Cloning: A Laboratory Manual $2^{nd}$ edition" (1989), Cold Spring Harbor Laboratory Press or the like.

Then, the invented protein will be described.

The invented protein can be produced, for example, by culturing a transformant comprising the invented DNA.

As a medium for culturing the transformant, for example, various media appropriately containing a carbon source or a nitrogen source, an organic salt or an inorganic salt, or the like which are normally used in culturing a host cell such as a microorganism can be used.

Examples of the carbon source include sugars such as glucose, dextrin and sucrose, sugar alcohols such as glycerol, organic acids such as fumaric acid, citric acid and pyruvic acid, animal oils, vegetable oils and beewax. The amount of these carbon sources to be added to a medium is usually around 0.1 to 30% (w/v) relative to the culturing solution.

Examples of the nitrogen source include natural organic nitrogen sources such as meat extract, peptone, yeast extract, malt extract, soybean powder, corn steep liquor, cottonseed powder, dry yeast and casamino acid, amino acids, ammonium salts of inorganic acids such as sodium nitrate, ammonium salts of inorganic acids such as ammonium chloride, ammonium sulfate and ammonium phosphate, ammonium salts of organic acids such as ammonium fumarate and ammonium citrate, and urea. Among them, ammonium salts of organic acids, natural organic nitrogen sources, amino acids and the like can also be used as a carbon source in many cases. The amount of these nitrogen sources to be added to a medium is usually around 0.1 to 30% (w/v) relative to the culturing solution.

Examples of the organic salts or the inorganic salts include chlorides, sulfates, acetates, carbonates and phosphates of potassium, sodium, magnesium, iron, manganese, cobalt, zinc and the like. Specific examples thereof include sodium chloride, potassium chloride, magnesium sulfate, ferrous sulfate, manganese sulfate, cobalt chloride, zinc sulfate, copper sulfate, sodium acetate, potassium carbonate, monopotassium hydrogen phosphate and dipotassium hydrogen phosphate. The amount of these organic salts and/or inorganic salts to be added to a medium is usually around 0.0001 to 5% (w/v).

Further, in the case of a transformant into which a gene in which a type of a promoter induced by allolactose such as a tac promoter, a trc promoter and a lac promoter, and the invented DNA are linked operably, as an induction agent for inducing production of the invented protein, for example, isopropyl thio-β-D-galactoside (IPTG) may be added to a medium at a small amount.

Culturing of a transformant comprising the invented DNA can be performed according to a method which is conventionally used in culturing a host cell such as a microorganism, and examples thereof include liquid culturing and solid culturing such as tube shaking culturing, reciprocating shaking culturing, jar fermenter culturing, tank culturing and the like.

A culturing temperature can be appropriately changed in such a range that the transformant can be grown, and is usually about 15 to 40° C. A pH of a medium is preferably in a range of about 6 to 8. A culturing time is different depending on the culturing condition and, usually, about 1 day to about 5 days is preferable.

As a method of purifying the invented protein from a culture of the transformant harboring the invented DNA, a method which is normally used in purification of a protein can be applied, and, for example, the following methods can be exemplified.

First, after cells are collected from a culture of the transformant by centrifugation or the like, these cells are ground by a physical grinding method such as ultrasonic treatment, dino mill treatment and French press treatment, or a chemical grinding method using surfactants or a bacteriolytic enzyme such as lysozyme. A cell-free extract is prepared by removing impurities from the resulting grinding solution by centrifugation, membrane filter filtration or the like, and this is fractionated by appropriately using a separation purification method such as cationic exchange chromatography, anion exchange chromatography, hydrophobic chromatography, gel filtration chromatography and metal chelate chromatography, whereby the invented protein can be purified.

Examples of a carrier used in chromatography include an insoluble polymer carrier such as cellulose, dextrin and agarose into which a carboxymethyl (CM) group, a diethylaminoethyl (DEAE) group, a phenyl group or a butyl group is introduced. A commercially available carrier-filled column may be used, and examples of the commercially available carrier-filled column include Q-Sepharose FF, Phenyl-Sepharose HP (trade name, both manufactured by Amersham Pharmacia Biotech), TSK-gel G3000SW (trade name, manufactured by Tosoh) and the like.

In order to select a fraction containing the invented protein, ortho-substituted phenylglyoxalic acid compound, for example, 2-(2-(2,5-dimethylphenoxymethyl)phenyl)-N-methyl-2-oxo-acetamide is asymmetrically reduced, and the fraction may be selected using, as an index, the ability to preferentially produce optically-active ortho-substituted mandelic acid compound, for example, (R)-2-(2-(2,5-dimethylphenoxymethyl)phenyl)-N-methyl-2-hydroxy-acetamide.

In the ortho-substituted phenylglyoxalic acid compound of the formula (1), and the ortho-substituted mandelic acid compound of the formula (2), $R_1$ will be described below.

Examples of an optionally substituted amino group represented by $R_L$ include, in addition to an amino group, a C1-6 alkylamino group such as a methlyamino group, an ethylamino group, a propylamino group, an isopropylamino group, a butylamino group, an isobutylamino group, a t-butylamino group, a pentylamino group, and a hexylamino group. In addition, examples of an optionally substituted alkoxy group include a C1-8 alkoxy group such as a methoxy group, an ethoxy group, a propoxy group, an isopropoxy group, a butoxy group, a pentyloxy group, a hexyloxy group, a heptyloxy group and an octyloxy group.

Then, a substituent represented by $R_2$ will be described below.

Examples of a C1-8 alkyl group in an optionally substituted C1-8 alkyl group represented by $R_2$ include a methyl group, an ethyl group, a propyl group, an isopropyl group, a butyl group, a pentyl group, a hexyl group, a heptyl group and an octyl group.

Examples of a substituent of such a C1-8 alkyl group include an optionally substituted alkoxy group and an optionally substituted aryloxy group.

Examples of an optionally substituted alkoxyalkyl group represented by $R_2$ include a C1-8 alkyl group substituted with a C1-4 alkoxy group such as a methoxymethyl group, a methoxyethyl group, a methoxypropyl group, a methoxybutyl group, a methoxypentyl group, a methoxyhexyl group, a methoxyheptyl group, a methoxyoctyl group, an ethoxymethyl group, an ethoxyethyl group, an ethoxypropyl group, an ethoxybutyl group, an ethoxypentyl group, an ethoxyhexyl group, an ethoxyheptyl group, an ethoxyoctyl group, a propoxymethyl group, a propoxyethyl group, a propoxypropyl group, a propoxybutyl group, a propoxypentyl group, a propoxyhexyl group, a propoxyheptyl group, a propoxyoctyl group, a butoxymethyl group, a butoxyethyl group, a butoxypropyl group, a butoxybutyl group, a butoxypentyl group, a butoxyhexyl group, a butoxyheptyl group and a butoxyoctyl group.

Examples of an optionally substituted aryloxy group include an aryloxy group represented by the formula (3):

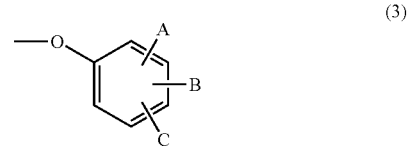

(wherein A, B and C are the same or different from one another, and represent a hydrogen atom, an alkyl group, an alkenyl group, an alkynyl group, a cycloakly group, a cycloalkenyl group, an alkoxy group, a halogenated alkyl group, a hydroxyalkyl group, an alkoxyalkyl group, an aminoalkyl group, an alkylaminoalkyl group, a halogen atom, a nitro group, a cyano group, an aralkyl group optionally substituted with an alkoxy group, an aryl group optionally substituted with a substituent selected from a halogen atom and an alkoxy group, an alkylthio group, an amino group, or an alkylamino group).

The substituent represented by A, B or C in the formula (3) will be described below.

Examples of the alkyl group include a C1-4 alkyl group such as a methyl group, an ethyl group, a propyl group, and a butyl group.

Examples of the alkenyl group include a C2-4 alkenyl group such as a vinyl group, an allyl group, and a crotyl group.

Examples of the alkynyl group include a C2-4 alkynyl group such as an ethynyl group, a propargyl group, and a butynyl group.

Examples of the cycloalkyl group include a C3-6 cycloalkyl group such as a cyclopropyl group, a cyclopentyl group, and a cyclohexyl group.

Examples of the cycloalkenyl group include a C5-6 cycloalkenyl group such as a cyclopentenyl group, and a cyclohexenyl group.

Examples of As the alkoxy group include a C1-4 alkoxy group such as a methoxy group, an ethoxy group, a propoxy group, and a butoxy group.

Examples of the halogenated alkyl group include a C1-3 haloalkyl group such as a trifluoromethyl group, a trichloromethyl group, a difluoromethyl group, a chloromethyl group, a 2-bromoethyl group, and a 1,2-dichloropropyl group.

Examples of the hydroxyalkyl group include a C1-2 alkyl group substituted with hydroxyl such as a hydroxymethyl group, and a 1-, 2-hydroxyethyl group.

Examples of the alkoxyalkyl group include a C1-2 alkyl group substituted with C1-2 alkoxy such as a methoxymethyl group, a methoxyethyl group, an ethoxymethyl group, and an ethoxyethyl group.

Examples of the aminoalkyl group include a C1-2 alkyl group substituted with monoamino, or a C1-2 alkyl group substituted with diamino, such as an aminomethyl group, and a 1-, 2-aminoethyl group.

Examples of the alkylaminoalkyl group include a C1-2 alkyl group substituted with (C1-2)alkylamino, or a C1-2 alkyl group substituted with di(C1-2)alkylamino, such as a methylaminomethyl group, a dimethylaminomethyl group, and h diethylaminomethyl group.

Examples of the halogen atom include a fluorine atom, a chlorine atom, a bromine atom, or an iodine atom.

Examples of the aralkyl group optionally substituted with an alkoxy group include a C7-8 aralkyl group optionally substituted with a C1-2 alkoxy group, such as a benzyl group, a phenethyl group, and a 4-methoxybenzyl group.

Examples of the aryl group optionally substituted with a group selected from a halogen atom and an alkoxy group include a C6-10 aryl group optionally substituted with a group selected from a halogen atom (fluorine atom, chlorine atom, bromine atom and iodine atom) and a C1-2 alkoxy group such as a 2-, 3-, 4-chlorophenyl group, a 2-, 3-, 4-methylphenyl group, a 2-, 3-, 4-methoxyphenyl group, a phenyl group, a 1-naphthyl group, and a 2-naphthyl group.

Examples of the alkylthio group include a C1-3 alkylthio group such as a methylthio group, an ethylthio group and a propylthio group.

Examples of the alkylamino group include a C1-6 alkylamino group such as a methylamino group, an ethylamino group, a propylamino group, an isopropylamino group, a butylamino group, an isobutylamino group, a t-butylamino group, a pentylamino group, and a hexylamino group.

From an ortho-substituted phenylglyoxalic acid compound having the optionally substituted aryloxy group and being represented by the formula (1'):

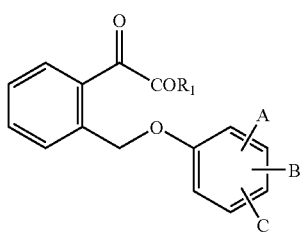

(wherein $R_1$ represents an optionally substituted amino group, or an optionally substituted alkoxy group, and A, B and C are the same or different from one another, and represent a hydrogen atom, an alkyl group, an alkenyl group, an alkynyl group, a cycloalkyl group, a cycloaklenyl group, an alkoxy group, a halogenated alkyl group, a hydroxyalkyl group, an alkoxyalkyl group, an aminoalkyl group, an alkylaminoalkyl group, a halogen atom, a nitro group, a cyano group, an aralkyl group optionally substituted with an alkoxy group, an aryl group optionally substituted with a substituent selected from a halogen atom and an alkoxy group, an alkylthio group, an amino group or an alkylamino group), a compound represented by the formula (2'):

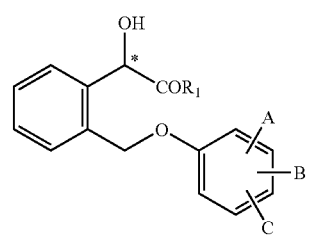

(wherein $R_1$, A, B and B are as defined above, and a hydrogen atom with a * symbol is an asymmetric carbon atom) is obtained.

In the compounds of the formula (1) and (1'), as the optionally substituted amino group represented by $R_1$, a methylamino group is preferable and, as the optionally substituted alkoxy group, for example, a methoxy group or an ethoxy group is preferable. In addition, as the optionally substituted C1-8 alkyl group represented by $R_2$, a methyl group is preferable, as the optionally substituted alkoxyalkyl group, for example, a methoxymethyl group is preferable, as the optionally substituted aryloxy alkyl group, for example, a dimethylphenoxymethyl group is preferable and, more particularly, 2-(2-methyl-phenyl)-N-methyl-2-oxo-acetamide, ethyl 2-(2-methyl-phenyl)oxoacetate, 2-(2-methoxymethyl-phenyl)-N-methyl-2-oxo-acetamide, ethyl 2-(2-methoxymethyl-phenyl)-2-oxoacetate, 2-(2-(2,5-dimethylphenoxymethyl)phenyl)-N-methyl-2-oxo-acetamide, or methyl 2-(2-(2,5-dimethylphenoxymethyl)phenyl)-2-oxoacetate is exemplified.

In the method of the present invention, when such an ortho-substituted phenylglyoxalic acid compound is a substrate, the compound of the formula (2) or the formula (2') is obtained, and as a specific compound, an optically-active substance of 2-(2-methyl-phenyl)-N-methyl-2-hydroxy-acetamide, ethyl 2-(2-methyl-phenyl)-2-hydroxy-acetate, 2-(2-methoxymethyl-phenyl)-N-methyl-2-hydroxy-acetamide, ethyl 2-(2-methoxymethyl-phenyl)-2-hydroxyacetate, 2-(2-(2,5-dimethylphenoxymethyl)phenyl)-N-methyl-2-hydroxy-acetamide, or methyl 2-(2-(2,5-dimethylphenoxymethyl)phenyl)-2-hydroxyacetate is obtained, respectively.

The method is usually performed in the presence of water, and a coenzyme such as reduced nicotineamide adenine dinucleotide phosphate (hereinafter, referred to as NADPH). The water used thereupon may be an aqueous buffer solution. Examples of a buffer used in the aqueous buffer solution include an alkali metal salt of phosphoric acid such as sodium phosphate and potassium phosphate, an aqueous sodium acetate solution, an alkali metal salt of acetic acid such as potassium acetate, and a mixture thereof.

In the method, in addition to water, an organic solvent may be present together. Examples of the organic solvent which may be present together include ethers such as t-butyl methyl ether, diisopropylether and tetrahydrofuran, esters such as ethyl formate, ethyl acetate, propyl acetate, butyl acetate, ethyl propionate and butyl propionate, hydrocarbons such as toluene, hexane, cyclohexane, heptane and isooctane, alcohols such as methanol, ethanol, 2-propanol, butanol and t-butyl alcohol, organic sulfur compounds such as dimethyl sulfoxide, ketones such as acetone, nitriles such as acetonitrile, and a mixture thereof.

For example, a reaction in the method is performed by mixing through stirring, shaking or the like in the state where water, an ortho-substituted phenylglyoxalic acid compound, and NADPH, together with the invented protein, or a transformant producing the same, or a treated product thereof and, if necessary, further an organic solvent or the like are contained.

A pH at a reaction in the method can be appropriately selected, and is usually in a range of a pH of 3 to 10. In addition, a reaction temperature can be appropriately selected, and is usually in a range of 0 to 60° C. from the viewpoint of stability of a raw material and a product, and a reaction rate.

An endpoint of the reaction can be determined, for example, by tracing the ortho-substituted phenylglyoxalic acid compound in the reaction solution by liquid chromatography or the like.

A reaction time can be appropriately selected, and is usually in a range of 0.5 hour to 10 days.

The recovery of an ortho-substituted optically active mandelic acid compound from the reaction solution may be performed by a generally known arbitrary method.

Examples thereof include a purification method by performing post-treatment such as organic solvent extraction operation and concentration operation of the reaction solution, if necessary, in combination with column chromatography, distillation or the like.

The invented protein, a transformant producing the same, or a treated product thereof can be used in the method in various forms.

Examples of the specific form of transformant or treated product thereof include a culture of a transformant comprising the invented DNA, and examples of the treated product of the transformant include a lyophilized transformant, an organic solvent-treated transformant, a dry transformant, a transformant ground product, a self-digestion product of a transformant, an ultrasonic-treated product of a transformant, a transformant extract, and an alkali-treated product of a transformant, a crude purified protein, a purified protein, and an immobilized product of enzyme protein. In addition, examples of a method of obtaining an immobilized product include a carrier binding method (a method of adsorbing the invented protein or the like onto an inorganic carrier such as silica gel and a ceramic, cellulose and an ion-exchanged resin), and an encapsulating method (a method of confining the invented protein or the like in a network structure of a polymer such as polyacrylamide, sulfur-containing polysaccharide gel (e.g. carrageenan gel), alginic acid gel and agar gel).

In addition, in view of industrial production using the transformant harboring the invented DNA, a method using a treated product obtained by killing the transformant is preferable rather than a method using a living transformant in that the restriction of a production facility is small. Examples of a method of kill treatment therefor include a physical sterilization method (heating, drying, freezing, light ray, ultrasound, filtration, powder distribution), and a sterilization method using a chemical (alkali, acid, halogen, oxidizing agent, sulfur, boron, arsenic, metal, alcohol, phenol, amine, sulfide, ether, aldehyde, ketone, cyan and antibiotic). Generally, it is desirable to select a treating method which inactivates enzyme activity of the invented protein as little as possible, and has little influence such as remaining in a reaction system, and contamination, among these sterilization methods.

In addition, a process of the present invention is performed in the presence of a coenzyme such as NADPH, in an ortho-substituted phenylglyoxalic acid compound, as an asymmetrical reducing reaction proceeds, the NADPH is converted into oxidized β-nicotineamide adenine dinucleotide phosphate (hereinafter, referred to as NADP$^+$) Since the NADP$^+$ generated by conversion can be returned to original NADPH by a protein having the ability to convert NADP$^+$ into reduced form (NADP), a protein having the ability to convert NADP$^+$ into NADPH can be present together in the reaction system of the method.

Examples of the protein having the ability to convert oxidized β-nicotineamide adenine dinucleotide (hereinafter, referred to as NAD$^+$), or NADP$^+$ into reduced β-nicotineamide adenine dinucleotide (hereinafter, referred to as NADH), or NADPH include glucose dehydrogenase, alcohol dehydrogenase, aldehyde dehydrogenase, amino acid dehydrogenase, organic dehydrogenase (malate dehydrogenase etc.) and the like.

In addition, when the protein having the ability to convert NAD$^+$, or NADP$^+$ into NADH, or NADPH is glucose dehydrogenase, by allowing glucose and the like to be present together in a reaction system, activity of the protein is enhanced in some cases, and these may be added, for example, to the reaction solution.

In addition, the protein may be an enzyme itself, or may be present together in the form of a microorganism having the enzyme, or a treated product of the microorganism in the reaction system.

Further, it may be a transformant containing a gene having a nucleotide sequence encoding an amino acid sequence of a protein having the ability to convert NAD$^+$, or NADP$^+$ into NADH, or NADPH, or a treated product thereof. Herein, the treated product means an equivalent of the aforementioned "treated product of a transformant".

Further, in the process for producing an optically-active ortho-substituted mandelic acid compound of the present invention, the process may also be performed using a transformant simultaneously comprising a DNA comprising a nucleotide sequence encoding an amino acid sequence of a protein having the ability to convert NAD$^+$, or NADP$^+$ into NADH, or NADPH such as glucose dehydrogenase, alcohol dehydrogenase, aldehyde dehydrogenase, amino acid dehydrogenase, and organic dehydrogenase (malate dehydrogenase etc.).

In this transformant, examples of a method of introducing both DNAs into a host cell include a method of introducing a single vector containing both DNAs into a host cell, a method of transforming a host cell with a recombinant vector in which both DNAs are separately introduced into a plurality of vectors having different replication origins, and the like. Further, one DNA or both DNAs may be introduced into a chromosome of a host cell.

In addition, as the method of introducing a single vector containing both DNAs into a host cell, for example, regions involved in expression control such as a promoter and a terminator may be connected to both DNAs to construct a recombinant vector, or a recombinant vector expressing a gene as an operon containing a plurality of cistrons such as lactose operon may be constructed.

EXAMPLES

Hereinafter, the present invention will be described in more detail by way of Examples or the like, but the present invention is not limited by those Examples at all.

Reference Example 1

Preparation of Chromosomal DNA

Each 100 ml of a medium (obtained by dissolving 2 g of glucose, 0.5 g of polypeptone, 0.3 g of yeast extract, 0.3 g of meat extract, 0.2 g of ammonium sulfate, 0.1 g of potassium dihydrogen phosphate, and 0.05 g of magnesium sulfate heptahydrate, and adjusting a pH to 6 with 2N HCl) was placed into two 500-ml flasks, and was sterilized at 121° C. for 15 minutes. To this was added each 0.3 ml of a culture of *Xanthomonas campestris* IFO13551 strain cultured (30° C., 48 hours, shaking culturing) in a medium of the same composition, followed by shaking culturing at 30° C. for 24 hours. Thereafter, the resulting culture was centrifuged (8000 rpm, 4° C., 10 minutes), and the resulting precipitate was collected. The precipitate was washed with 50 ml of a 0.85% aqueous sodium chloride solution to obtain about 3 g of wet bacterial cells.

From the bacterial cell, a chromosomal DNA (hereinafter, referred to as chromosomal DNA (A)) was obtained by using QIAprep Genomic-tip System (manufactured by Qiagen).

Example 1

Obtaining of Invented DNA, and Analysis Thereof

Based on the amino acid sequence shown in SEQ ID NO: 3, presumed reductase gene (GenBank accession numbers: AE012123 (region: 2600-3568)) of *Xanthomonas campestris* pv. *campestris* ATCC33913 strain, an oligonucleotide primer comprising the nucleotide sequence shown in SEQ ID NO:4 and an oligonucleotide primer comprising the nucleotide sequence shown in SEQ ID NO:5 were synthesized.

Using the oligonucleotide primers each having the nucleotide sequences shown in SEQ ID NO: 4 and SEQ ID NO: 5, and employing the chromosomal DNA (A) as a template, PCR was performed under the following reaction solution composition and the reaction condition (using Expand High Fidelity PLUS PCR System manufactured by Roche Diagnostics).

[Reaction Solution Composition]

| Chromosomal DNA (A) solution | 2 μl |
|---|---|
| dNTP (each 2.5 mM-mix) | 1 μl |
| Primer (50 pmol/μl) | each 0.4 μl |
| 5 × buffer (with MgCl) | 10 μl |
| enz. expandHiFi (5 U/μl) | 0.5 μl |
| Superpure water | 35.7 μl |

[Reaction Condition]

A container containing a reaction solution of the above composition was set in PERKIN ELMER-GeneAmp PCR System 9700, and was heated at 94° C. for 2 minutes, followed by 10 times of a cycle of 94° C. (10 seconds)-65° C. (30 seconds)-72° C. (90 seconds) and, then, 20 times of a cycle of 94° C. (10 seconds)-65° C. (30° C. seconds)-72° C. (1 minute+5 second/cycle), and further, the container was incubated at 72° C. for 7 minutes.

Thereafter, an aliquot of the PCR reaction solution was taken and was subjected to agarose gel electrophoresis resulting in detecting a band of a DNA fragment of about 1000 bp.

The DNA fragment of about 600 bp was ligated to the ready-made "PCR Product insertion site" of a pCR2.1-TOPO vector (using TOPO TA cloning Kit, manufactured by Invitrogen), and *E. coli* TOP10F' was transformed with the resulting ligation solution.

Thirty (30) μl of a 4% aqueous solution of 5-bromo-4-chloro-3-indolyl β-D-galactoside (hereinafter, referred to as X-gal) and 30 μl of 0.1 M IPTG were spread on an LB (1% Bacto-trypsin, 0.5% Bacto-yeast extract, 1% sodium chloride) agar medium containing 50 μg/ml of ampicillin, and the resulting transformants were inoculated thereon, followed by culturing. Eight white colonies among formed colonies were taken, and this colony was inoculated in a sterilized LB medium (2 ml) containing 50 μg/ml of ampicillin, and shaking-cultured (30° C., 24 hours) in a tube. A plasmid was taken out from the cultured bacterium cells using QIAprep Spin Miniprep Kit (manufactured by Qiagen).

A nucleotide sequence of the DNA fragment having been inserted into the resulting plasmid was analyzed. Based on the resulting nucleotide sequence, was determined the nucleotide sequence (SEQ ID NO: 2) encoding an amino acid sequence of a protein of *Xanthomonas campestris* IFO13551 strain having the ability to asymmetrically reduce 2-(2-(2,5-dimethylphenoxymethyl)phenyl)-N-methyl-2-oxo-acetamide to preferentially produce (R)-2-(2-(2,5-dimethylphenoxymethyl)phenyl)-N-methyl-2-hydroxy-acetamide. Further, based on SEQ ID NO: 2, the amino acid sequence (SEQ ID NO: 1) of the protein was determined. The analysis of the nucleotide sequence of the DNA fragment inserted in the plasmid was performed by conducting a sequencing reaction using Dye Terminator Cycle sequencing FS ready Reaction Kit (manufactured by Perkin Elmer) and employing each plasmid as a template, and analyzing the nucleotide sequence of the resulting DNA with a DNA Sequencer 373A (manufactured by Perkin Elmer).

Example 2

Example of Production of Invented Transformant and Reducing Reaction (1))

(1) Preparation of Invented Vector

Based on the nucleotide sequence shown in SEQ ID NO: 2, an oligonucleotide primer comprising the nucleotide sequence shown in SEQ ID NO: 6, and an oligonucleotide primer comprising the nucleotide sequence shown in SEQ ID NO: 7 were synthesized.

Using the oligonucleotide primer comprising the nucleotide sequence shown in SEQ ID NO: 6, and the oligonucleotide primer shown in SEQ ID NO: 7 as primers, and employing the chromosomal DNA (A) as a template, PCR was performed under the following reaction solution composition and the reaction condition (using Expand High Fidelity PLUS PCR System manufactured by Roche Diagnostics).

[Reaction Solution Composition]

| Chromosomal DNA (A) solution | 2 μl |
|---|---|
| dNTP (each 2.5 mM-mix) | 1 μl |
| Primer (50 pmol/μl) | each 0.4 μl |
| 5 × buffer (with MgCl) | 10 μl |
| enz. expandHiFi (5 U/μl) | 0.5 μl |
| Superpure water | 35.7 μl |

A container containing a reaction solution of the above composition was set in PERKIN ELMER-GeneAmp PCR System 9700, and was heated at 94° C. for 2 minutes, followed by 10 times of a cycle of 94° C. (10 seconds)-65° C. (30 seconds)-72° C. (90 seconds), and then, 20 times of a cycle of 94° C. (10 seconds)-65° C. (30 seconds)-72° C. (1 minute+5 seconds/cycle), and further, the container was incubated at 72° C. for 7 minutes.

Thereafter, an aliquot of the PCR reaction solution was taken and subjected to agarose gel electrophoresis resulting in detection of a band of a DNA fragment of about 1000 bp.

Two kinds of restriction enzymes (NcoI and XbaI) were added to the remaining PCR reaction solution to double-digest the DNA fragment of about 1000 bp, and then, the enzyme-digested DNA fragment was purified.

Separately, a plasmid vector pTrc99A (manufactured by Pharmacia) was double-digested with two kinds of restriction enzymes (NcoI and XbaI), and the enzyme-digested DNA fragment was purified.

These enzyme-digested DNA fragments were mixed, and ligated with a T4 DNA ligase, and *E. coli* DH5α was transformed with the resulting ligation solution.

The resulting transformants were cultured on an LB agar medium containing 50 µg/ml of ampicillin, and 2 colonies were randomly selected from the grown colonies. Each of the selected colonies was inoculated in a sterilized LB medium (2 ml) containing 50 µg/ml of ampicillin, and shaking-cultured (37° C., 17 hours) in a tube.

A plasmid was taken out from each cultured bacterial cell using QIAprep Spin Miniprep Kit (manufactured by Qiagen). An aliquot of each plasmid taken out was double-digested with two kinds of restriction enzymes of NcoI and XbaI, and then subjected to electrophoresis to confirm that the DNA fragment of about 1000 bp was inserted in each of the six plasmids taken out (hereinafter, this plasmid is referred to as plasmid pTrcRxc).

(2) Example of Preparation of Invented Transformant and Reducing Reaction

*E. coli* HB101 was transformed using the plasmid pTrcRxc. The resulting transformant was inoculated in a sterilized LB medium (5 ml) containing 0.1 mM of IPTG and 50 µg/ml of ampicillin, and shaking-cultured (370° C., 15 hours). The resulting culture was centrifuged to obtain 0.09 g of wet bacterial cells. The resulting wet bacterial cells were mixed with 1.5 mg of 2-(2-(2,5-dimethylphenoxymethyl) phenyl)-N-methyl-2-oxo-acetamide, 6.9 mg of NADPH, 1.5 ml of a 100 mM phosphate buffer (pH 7.0), 2.7 mg of glucose, and 0.075 ml of butyl acetate, followed by stirring at 30° C. for 23 hours. Thereafter, 2 ml of ethyl acetate was added to the reaction solution, and this was centrifuged to obtain an organic layer. The organic layer was subjected to content analysis by liquid chromatography under the following condition, and it was found that 2-(2-(2,5-dimethylphenoxymethyl)phenyl)-N-methyl-2-hydroxy-ace tamide was produced at 97.9% relative to the amount of 2-(2-(2,5-dimethylphenoxymethyl)phenyl)-N-methyl-2-oxo-acetamide used in the reaction. The optical purity of 2-(2-(2, 5-dimethylphenoxymethyl)phenyl)-N-methyl-2-hydroxy-ace tamide in the organic layer was measured under the following condition. The optical purity of (R) body was found to be 100% e.e.

(Content Analysis Condition)

Column: SUMICHIPRAL ODS A-212

Mobile phase; A solution 0.1% aqueous trifluoroactic acid solution, B solution acetonitrile solution containing 0.1% trifluoroactic acid

| Time (min) | A solution (%):B solution (%) |
|---|---|
| 0 | 80:20 |
| 20 | 10:90 |

-continued

| Time (min) | A solution (%):B solution (%) |
|---|---|
| 30 | 1:99 |
| 30.1 | 80:20 |

Flow rate: 0.5 ml/min
Column temperature: 40° C.
Detection: 290 nm
(Optical purity measuring condition)
Column: CHIRALCEL OD-H
Mobile phase: hexane:2-propanol = 9:1
Analysis time: 50 minutes
Flow rate: 0.5 ml/min
Column temperature: 40° C.
Detection: 230 nm Example 3

Example of Production of Invented Transformant and Reducing Reaction (2)

(1) Arrangement for Preparing a Gene Comprising a Nucleotide Sequence Encoding an Amino Acid Sequence of a Protein Having Ability to Convert Oxidized β-Nicotineamide Adenine Dinucleotide into Reduced Form

*Bacillus megaterium* IFO12108 strain was cultured in 100 ml of a sterilized LB medium to obtain 0.4 g of bacterial cells. From the bacterial cells, a chromosomal DNA (hereinafter, referred to as chromosomal DNA (B)) was purified using Qiagen Genomic Tip (manufactured by Qiagen) according to the method described in a manual attached thereto.

(2) Preparation of a Gene Comprising a Nucleotide Sequence Encoding an Amino Acid Sequence of a Protein Having Ability to Convert Oxidized β-Nicotineamide Adenine Dinucleotide into Reduced Form Based on the sequence of glucose dehydrogenase derived from *Bacillus megaterium* IWG3 described in The Journal of Biological Chemistry Vol. 264, No. 11, 6381-6385 (1989), an oligonucleotide primer comprising the nucleotide sequence shown in SEQ ID NO: 8, and an oligonucleotide primer comprising the nucleotide sequence shown in SEQ ID NO: 9 were synthesized.

Using the oligonucleotide primer comprising the nucleotide sequence shown in SEQ ID NO: 8 and the oligonucleotide primer comprising the nucleotide sequence shown in SEQ ID NO: 9 as primers, and employing the chromosomal DNA (B) as a template, PCR was performed under the following reaction solution composition and the reaction condition (using Expand High Fidelity PCR System manufactured by Roche Diagnostics).

[Reaction Solution Composition]

| | |
|---|---|
| Chromosomal DNA (B) stock solution | 1 µl |
| dNTP (each 2.5 mM-mix) | 0.4 µl |
| Primer (20 pmol/µl) | each 0.75 µl |
| 10 × buffer (with MgCl) | 5 µl |
| enz. expandHiFi (3.5 × $10^3$ U/ml) | 0.375 µl |
| Superpure water | 41.725 µl |

[PCR Reaction Condition]

A container containing a reaction solution of the above composition was set in PERKIN ELMER-GeneAmp PCR System2400, and was heated at 97° C. for 2 minutes, followed by 10 times of a cycle of 97° C. (15 seconds)-55° C. (30 seconds)-72° C. (1.5 minutes), and then, 20 times of a cycle of 97° C. (15 seconds)-55° C. (30 seconds)-72° C. (1 minute+5 seconds/cycle), and further, the container was incubated at 72° C. for 7 minutes.

Thereafter, an aliquot of the PCR reaction solution was taken, and subjected to agarose gel electrophoresis resulting in detection of a band of a DNA fragment of about 950 bp.

The DNA fragment of about 950 bp obtained by PCR was ligated with the ready-made "PCR Product insertion site" of pCR2.1-TOPO vector using the resulting PCR reaction solution and TOPO TA cloning Kit Ver. E manufactured by Invitrogen, and E. coli DH5α was transformed with the ligation solution.

Thirty (30) μg of an X-gal 4% aqueous solution and 30 μl of 0.1M IPTG were spread on an LB agar medium containing 50 μg/ml of ampicillin, and the resulting transformants were inoculated thereon, followed by culturing. One white colony among formed colonies was taken, and this colony was inoculated in a sterilized LB medium (2 ml) containing 50 g/ml of ampicillin, and this was shaking-cultured (30° C., 24 hours) in a tube. Then, a plasmid was taken out from the cultured bacterial cells using QIAprep Spin Miniprep Kit (manufactured by Qiagen). An aliquot of the plasmid taken out was digested with the restriction enzyme (EcoRI), and it was subjected to electrophoresis, whereby it was confirmed that the DNA fragment of about 950 bp was inserted in the plasmid (hereinafter, this plasmid is referred to as plasmid pSDGDH12).

A nucleotide sequence of the DNA fragment having been inserted in the Plasmid pSDGDH12 was analyzed. The result is shown in SEQ ID No: 10.

The analysis of the nucleotide sequence of the DNA fragment having been inserted in the plasmid was performed by conducting a sequencing reaction using Dye Terminator Cycle sequencing FS ready Reaction Kit (manufactured by Perkin Elmer), and employing the Plasmid pSDGDH12 as a template, and analyzing the nucleotide sequence of the resulting DNA with DNA Sequencer 373A (manufactured by Perkin Elmer).

Then, based on the nucleotide sequence shown in SEQ ID NO: 10, oligonucleotide primers comprising the nucleotide sequences shown in SEQ ID NO: 11 and SEQ ID NO: 12 were synthesized.

PCR was performed using the oligonucleotide primes having the nucleotide sequences shown in SEQ ID NO: 11 and SEQ ID NO 12, and employing the chromosomal DNA (B) under the following reaction solution composition and the reaction condition (using Expand High Fidelity PCR System manufactured by Roche Diagnostics).

[Reaction Solution Composition]

| | |
|---|---|
| Chromosomal DNA (B) stock solution | 1 μl |
| dNTP (each 2.5 mM-mix) | 0.4 μl |
| Primer (20 pmol/μl) | each 0.75 μl |
| 10 × buffer (with MgCl) | 5 μl |
| enz. expandHiFi (3.5 × 10³ U/ml) | 0.375 μl |
| Superpure water | 41.725 μl |

[PCR Reaction Condition]

A container containing a reaction solution of the above composition was set in PERKIN ELMER-GeneAmp PCR System2400, and was heated at 97° C. for 2 minutes, followed by 10 times of a cycle of 97° C. (15 seconds)-55° C. (30 seconds)-72° C. (1.5 minutes), and then, 20 times of a cycle of 97° C. (15 seconds)-55° C. (30 seconds)-72° C. (1 minute+5 seconds/cycle), and then, the container was incubated at 72° C. for 7 minutes.

Thereafter, an aliquot of the PCR reaction solution was taken, and subjected to agarose gel electrophoresis resulting in detection of a band of a DNA fragment of about 800 bp.

Two kinds of restriction enzymes (NcoI and BamHI) were added to the remaining PCR reaction solution to double-digest the DNA fragment of about 800 bp, and then, the enzyme-digested DNA fragment was purified.

Separately, the plasmid vector pTrc99A (manufactured by Pharmacia) was double-digested with two kinds of restriction enzymes (NcoI and BamHI), and the enzyme-digested DNA fragment was purified.

These enzyme-digested DNA fragments were mixed, and ligated with a T4 DNA ligase, and E. coli DH5α was transformed with the resulting ligation solution.

The resulting transformants were cultured on an LB agar medium containing 50 μg/ml of ampicillin, and 10 colonies were randomly selected from the grown colonies. Each of the selected colonies was inoculated in a sterilized LB medium (2 ml) containing 50 μg/ml of ampicillin, and this was shaking-cultured (37° C., 17 hours) in a tube. A plasmid was taken out from each cultured bacterial cell using QIAprep Spin Miniprep Kit (manufactured by Qiagen). An aliquote of each plasmid taken out was double-digested with two kinds of restriction enzymes of NcoI and BamHI, and then subjected to electrophoresis to confirm that the DNA fragment of about 800 bp was inserted in each of four plasmids taken out (hereinafter, this plasmid is referred to as Plasmid pTrcGDH).

(3) Preparation of Invented Vector

Using as primers an oligonucleotide primer comprising the nucleotide sequence shown in SEQ ID NO: 13 and an oligonucleotide primer shown in SEQ ID NO: 7, and employing the plasmid pTrcRxc as a template, PCR was performed under the following reaction solution composition and the reaction condition (using Expand High Fidelity PCR System manufactured by Roche Diagnostics).

[Reaction Solution Composition]

| | |
|---|---|
| Plasmid pTrcRs | 2 μl |
| dNTP (each 2.5 mM-mix) | 1 μl |
| Primer (50 pmol/μl) | each 0.4 μl |
| 5 × buffer (with MgCl) | 10 μl |
| Expand High Fidelity PLUS Taq polymerase | 0.5 μl (2.5 U) |
| Superpure water | 35.7 μl |

[Reaction Condition]

A container containing a reaction solution of the above composition was set in PERKIN ELMER-GeneAmp PCR System 9700, and was heated at 94° C. for 2 minutes, followed by 10 times of a cycle of 94° C. (10 seconds)-65° C. (30 seconds)-72° C. (90 seconds), and then, 20 times of a cycle of 94° C. (10 seconds)-65° C. (30 seconds)-72° C. (1 minute+5 seconds/cycle), and further, the container was incubated at 72° C. for 7 minutes.

Thereafter, an aliquote of the PCR reaction solution was taken, and subjected to agarose gel electrophoresis resulting in detection of a band of a DNA fragment of about 1000 bp.

Two kinds of restriction enzymes (BamH and XbaI) were added to the remaining PCR reaction solution to double-digest the DNA fragment of about 1000 bp, and then, the enzyme-digested DNA fragment was purified.

Separately, the plasmid pTrcGDH was double-digested with two kinds of restriction enzymes (BamHI and XbaI), and the enzyme-digested DNA fragment was purified.

These enzyme-digested DNA fragments were ligated with a T4 DNA ligase, and E. coli DH5α was transformed with the ligation solution. The resulting transformants were cultured on an LB agar medium containing 50 μg/ml of ampicillin, and 6 colonies were randomly selected from grown colonies. Each of the selected colonies was inoculated in a sterilized LB medium (2 ml) containing 50 μg/ml of ampicillin, and shaking-cultured (30° C., 7 hours) in a tube. A plasmid was taken out from each cultured bacterial cell using QIAprep Spin Miniprep Kit (manufactured by Qiagen). An aliquote of each plasmid taken out was double-digested with two kinds of restriction enzymes of BamHI and XbaI, and then subjected to electrophoresis to confirm that the DNA fragment of about 1000 bp of interest was inserted in all of the plasmid taken out (hereinafter, this plasmid is referred to as plasmid pTrcG-SRxc).

(4) Example of Preparation of Invented Transformant and Reducing Reaction

Using the plasmid pTrcGSRs, *E. coli* HB101 was transformed. The resulting transformant was inoculated in a sterilized LB medium (5 ml) containing 0.2 mM of IPTG and 50 μg/ml of ampicillin, and shaking-cultured (30° C., 24 hours). The resulting culture was centrifuged to obtain about 0.3 g of wet bacterial cells. The resulting wet bacterial cells were mixed with 1.5 mg of 2-(2-(2,5-dimethylphenoxymethyl)phenyl)-N-methyl-2-oxo-acetamide, 6.9 mg of NADPH, 1.5 ml of 100 mM phosphate buffer (pH 7.0), 2.7 mg of glucose, and 0.075 ml of butyl acetate, followed by stirring at 30° C. for 24 hours. Thereafter, 2 ml of ethyl acetate was added to the reaction solution, and this was centrifuged to obtain an organic layer. The organic layer was subjected to content analysis by liquid chromatography under the following condition, and it was found that 2-(2-(2,5-dimethylphenoxymethyl)phenyl)-N-methyl-2-hydroxy-acetamide is produced at 100% relative to the amount of 2-(2-(2,5-dimethylphenoxymethyl)phenyl)phenyl)-N-methyl-2-oxo-acetamide used in the reaction. The optical purity of 2-(2-(2,5-dimethylphenoxymethyl)phenyl)-N-methyl-2-hydroxy-acetamide in the organic layer was measured under the following condition. The optical purity of (R) body was found to be 100% e.e.

(Content Analysis Condition)
Column: SUMICHIRAL ODS A-212
Mobile phase: A solution 0.1% aqueous trifluoroacetic acid solution, B solution acetonitrile solution containing 0.1% trifluoroacetic acid

| Time (min) | A solution (%):B solution (%) |
|---|---|
| 0 | 80:20 |
| 20 | 10:90 |
| 30 | 1:99 |
| 30.1 | 80:20 |

Flow rate: 0.5 ml/min
Column temperature: 40° C.
Detection: 290 nm
(Optical purity measuring condition)
Column: CHIRALCEL OD-H
Mobile phase: hexane:2-propanol = 9:1
Analysis time: 50 minutes
Flow rate: 0.5 ml/min
Column temperature: 40° C.
Detection: 230 nm Example 4

Example of Reducing Reaction by Invented Transformant (3))

Using the plasmid pTrcRxc, *E. coli* HB101 was transformed. The resulting transformant was inculcated in a sterilized LB medium (5 ml) containing 0.2 mM of IPTG and 50 μg/ml of ampicillin, and shaking-cultured (37° C., 15 hours). The resulting culture was centrifuged to obtain about 0.3 g of wet bacterial cells. The resulting wet bacterial cells were mixed with 1.5 mg of methyl 2-(2-(2,5-dimethylphenoxymethyl)phenyl)-2-oxoacetate, 6.9 mg of NADPH, 2.7 mg of glucose, 1.5 ml of 100 mM phosphate buffer (pH 7.0), and 0.075 ml of butyl acetate, followed by stirring at 30° C. for 24 hours. Thereafter, 2 ml of ethyl acetate was added to the reaction solution, and this was centrifuged to obtain an organic layer. The organic layer was subjected to content analysis by liquid chromatography under the following condition, and it was found that methyl 2-(2-(2,5-dimethylphenoxymethyl)phenyl)-2-hydroxyacetate is produced at 95.2% relative to the amount of methyl 2-(2-(2,5-dimethylphenoxymethyl)phenyl)-2-oxoacetate used in the reaction. The optical purity of methyl 2-(2-(2,5-dimethylphenoxymethyl)phenyl)-2-hydroxyacetate in the organic layer was measured under the following condition. The optical purity of (R) body was found to be 100% e.e.

(Content Analysis Condition)
Column: SUMICHIRAL ODS A-212
Mobile phase: A solution 0.1% aqueous trifluoroacetic acid solution, B solution acetonitrile solution containing 0.1% trifluoroacetic acid

| Time (min) | A solution (%):B solution (%) |
|---|---|
| 0 | 80:20 |
| 20 | 10:90 |
| 30 | 1:99 |
| 30.1 | 80:20 |

Flow rate: 0.5 ml/min
Column temperature: 40° C.
Detection: 290 nm
(Optical purity measuring condition)
Column: CHIRALCEL OD-H
Mobile phase: hexane:2-propanol = 9:1
Analysis time: 50 minutes
Flow rate: 0.5 ml/min
Column temperature: 40° C.
Detection: 230 nm Example 5

Example of Reducing Reaction by Invented Transformant (4))

(1) Synthesis of ethyl 2-(2-methyl-phenyl)-2-oxoacetate

To a mixture of 50 g of tatrahydrofuran and 7.3 g of magnesium was added 4.4 g of 2-bromotoluene to activate the magnesium. A temperature was raised to 40° C., a solution of 45 g of 2-bromotoluene intetrahydrofuran (130 g) was added dropwise until the disappearance of 2-bromotoluene was confirmed. Thereafter, the mixture was cooled to room temperature to prepare a Grignard reagent.

A solution of 83 g of diethyl oxalate in toluene (170 g) was cooled to −40° C. or lower. The Grignard reagent prepared as described above was added dropwise at −40° C. or lower, and this was retained at −40° C. for 2 hours. To the reaction mixture was added 234 g of 10% sulfuric acid, and an organic layer was recovered. The resulting organic layer was washed with 134 g of water, and dried with magnesium sulfate. After concentration with an evaporator, distillation under high vacuum, and silica gel column purification afforded 33.1 g of ethyl 2-(methyl-phenyl)-2-oxoacetate.

¹H-NMR (300 MHz, CDCl₃): δ ppm: 1.41 (t, J=7.2 Hz, 3H), 2.61 (s, 3H), 4.39-4.47 (m, 2H), 7.26-7.70 (m, 4H)

(2) Synthesis of 2-(2-methyl-phenyl)-N-methyl-2-oxo-acetamide

The ethyl 2-(2-methyl-phenyl)-2-oxoacetate of 18.1 g obtained in (1), 72 g of toluene, and 36 g of methanol were mixed, 23.2 g of a 40% aqueous methylamine solution was added while retaining at 25° C., and the mixture was retained at 25° C. for 1 hour. Thereafter, 36.2 g of water was added, and an organic layer was recovered. The layer was washed with 143 g of 5% hydrochloric acid, 360 g of an aqueous saturated sodium bicarbonate solution, and 36 g of water, respectively, and dried with magnesium sulfate. After concentration with an evaporator, silica gel column purification afforded 11.4 g of 2-(2-methyl-phenyl)-N-methyl-2-oxo-acetamide.

¹H-NMR (300 MHz, CDCl₃): δ ppm: 2.48 (s, 3H), 2.96 (d, J=5.13 Hz, 3H), 7.1 (6 s, 1H), 7.25-7.93 (m, 4H)

(3) Asymmetrical reduction of 2-(2-methyl-phenyl)-N-methyl-2-oxo-acetamide using Invented Transformant Using the plasmid pTrcGSRxc, *E. coli* HB101 was transformed. The resulting transformant was inoculated in a sterilized LB medium (100 ml) containing 0.1 mM of IPTG and 50 μg/ml of ampicillin, and was shaking-cultured (37° C., 15 hours). The resulting culture was centrifuged to obtain 0.1 g of wet bacterial cells. To a reaction tube were added 1.5 mg of 2-(2-methyl-phenyl)-N-methyl-2-oxo-acetamide, 0.1 g of the wet bacterial cells, 10 mg of NADPH, and 1.5 ml of a 100 mM phosphate buffer solution (pH 7), and these were reacted at a stirring rate of 1000 rpm at 30° C. for 20 hours. After the completion of the reaction, 5 ml of ethyl acetate was added to the reaction solution, and this was centrifuged (1000×g, 5 minutes) to recover an organic layer. The organic layer was distilled off to obtain oily 2-(2-methyl-phenyl)-N-methyl-2-hydroxy-acetamide. Content analysis by liquid chromatography under the following condition showed that the conversion rate was 87.2%. ¹H-NMR analysis result of the resulting 2-(2-methyl-phenyl)-N-methyl-2-hydroxy-acetamide is shown below.

¹H-NMR (300 MHz, CDCl₃) σ 2.37 (S, 3H), 2.79 (d, J=4.96 Hz, 3H), 3.87 (1H), 5.15 (S, 1H), 6.21 (S, 1H), 7.15-7.26 (m, 4H)
(Content Analysis Condition)
Column: SUMICHIRAL ODS A-212
Mobile phase: A solution 0.1% aqueous trifluoroacetic acid solution, B solution acetonitrile solution containing 0.1% trifluoroacetic acid

| Time (min) | A solution (%):B solution (%) |
|---|---|
| 0 | 80:20 |
| 20 | 10:90 |
| 30 | 1:99 |
| 30.1 | 80:20 |

Flow rate: 0.5 ml/min
Column temperature: 40° C.
Detection: 290 nm
Elusion time
2-(2-methyl-phenyl)-N-methyl-2-oxo-acetamide: 18.4 minutes To the resulting ethyl 2-(2-methyl-phenyl)-2-hydroxy-acetate was added hexane containing 10% 2-propanol, optical purity of 2-(2-methyl-phenyl)-N-methyl-2-hydroxy-acetamide in organic layer was measured under the following condition, and the optical purity was found to be 100% e.e. (elution time: 23.4 minutes).

Racemic 2-(2-methyl-phenyl)-N-methyl-2-hydroxy-acetamide was synthesized by reducing 2-(2-methyl-phenyl)-N-methyl-2-oxo-acetamide with NaBH₄ in methanol.
(Optical Isomer Analysis Condition)
Column: CHIRALPAK OD-H (manufactured by Daicel Chemical Industries)
Mobile phase: hexane/2-propanol-90/10
Flow rate: 0.5 ml/min
Column temperature: 40° C.
Detection: 230 nm
Elusion time
2-(2-methyl-phenyl)-N-methyl-2-oxo-acetamide: 16.0 minutes
2-(2-methyl-phenyl)-N-methyl-2-hydroxyacetamide: 20.1 minutes, 23.3 minutes Example 6

Example of Reducing Reaction by Invented Transformant (5)

A reaction was performed according to the same manner as in Example 5 except that ethyl 2-(2-methyl-phenyl)-2-oxoacetate was used as a substrate. As a result, oily ethyl 2-(2-methyl-phenyl)-2-hydroxy-acetate was obtained. Content analysis by liquid chromatography under the following condition showed that the conversion rate was 97.5%. ¹H-NMR analysis result of the resulting ethyl 2-(2-methyl-phenyl)-2-hydroxy-acetate is shown below.

¹H-NMR (300 MHz, CDCl₃) σ 1.21 (t, J=7.2 Hz, 3H), 2.43 (S, 3H), 3.56 (d, J=7.7 Hz, 1H), 4.13-4.29 (m, 2H), 5.35 (S, 1H), 7.15-7.30 (m, 4H)
(Content Analysis Condition)
Column: SUMICHIRAL ODS A-212
Mobile phase: A solution 0.1% aqueous trifluoroacetic acid solution, B solution acetonitrile solution containing 0.1% trifluoroacetic acid

| Time (min) | A solution (%):B solution (%) |
|---|---|
| 0 | 80:20 |
| 20 | 10:90 |
| 30 | 1:99 |
| 30.1 | 80:20 |

Flow rate: 0.5 ml/min
Column temperature: 40° C.
Detection: 290 nm
Elusion time
ethyl 2-(2-methyl-phenyl)-2-oxoacetamide: 17.1 minutes To the resulting ethyl 2-(2-methyl-phenyl)-2-hydroxy-acetate was added hexane containing 10% 2-propanol, this was subjected to optical purity analysis by liquid chromatography under the following condition, and an optical purity was found to be 99% e.e. (elution time: 13.7 minutes).

Racemic ethyl 2-(2-methyl-phenyl)-2-hydroxy-acetate was synthesized by reducing ethyl 2-(2-methyl-phenyl)-2-oxoacetate with NaBH₄ in methanol.
(Optical Isomer Analysis Condition)
Column: CHIRALPAK OD-H (manufactured by Daicel Chemical Industries)

Mobile phase: hexane/2-propanol=90/10
Flow rate: 0.5 ml/min
Column temperature: 40° C.
Detection: 230 nm
Elusion time
  ethyl 2-(2-methyl-phenyl)-2-oxoacetate: 9.1 minutes
  ethyl 2-(2-methyl-phenyl)-2-hydroxy-acetate: 11.8 minutes, 13.6 minutes Example 7

Example of Reducing Reaction by Invented Transformant (6)

(1) Synthesis of ethyl 2-(2-methoxymethyl-phenyl)-2-oxoacetate

A temperature of 59.8 g of a 28% solution of sodium methoxide in methanol was raised to 60° C., a mixture solution of 70.4 g of o-bromobenzyl bromide and 70.4 g of methanol was added dropwise, and this was retained at 60° C. for 2 hours. After the mixture was cooled to room temperature, 211 g of toluene and 211 g of water were added thereto, the mixture was stirred, and layers were separated, and an organic layer was recovered. An aqueous layer was extracted with 211 g of toluene three times, the recovered organic layer and 211 g of water were added, and this was washed, and concentrated to obtain 55.3 g of 1-methoxymethyl-2-bromobenzene.

To a mixture of 46.4 g of tetrahydrofuran and 5.4 g of magnesium was added 4.6 g of 1-methoxymethyl-2-bromobenzene to activate the magnesium. A temperature was raised to 40° C., a solution of 41.7 g of 1-methoxymethyl-2-bromobenzene in tetrahydrofuran (139 g) was added dropwise until the disappearance of 1-methoxymethyl-2-bromobenzene was confirmed. Thereafter, the mixture was cooled to room temperature to prepare a Grignard agent.

A solution of 64.4 g of diethyl oxalate in toluene (177 g) was cooled to −40° C. or lower. The Grignard agent prepared as described above was added dropwise at −40° C. or lower, and this was retained at −40° C. for 4 hours. To the reaction mixture was added 211 g of 10% sulfuric acid, and an organic layer was recovered. The resulting organic layer was washed with 133 g of water, and dried with magnesium sulfate. After concentration with an evaporator, silica gel column purification and distillation under the high pressure afforded 38.5 g of ethyl 2-(2-methoxymethyl-phenyl)-2-oxoacetate.

$^1$H-NMR (300 MHz, CDCl$_3$): δ ppm: 1.41 (t, J=7.08 Hz, 3H), 3.44 (s, 3H), 4.41 (q, 2H), 4.75 (s, 2H), 7.55-7.69 (m, 4H)

(2) Synthesis of 2-(2-methoxymethyl-phenyl)-N-methyl-2-oxo-acetamide 28.3 g of the ethyl 2-(2-methoxymethyl-phenyl)-2-oxoacetate obtained in (1), 109 g of toluene, and 54.4 g of methanol were mixed, 28.6 g of a 40% aqueous methylamine solution was added while retaining at 25° C., and the mixture was retained at 25° C. for 2 hours. Thereafter, 54.4 g of water was added, 80 g of toluene were further added, this was allowed to stand still, and an organic layer was recovered. The organic layer was washed with 178 g of 5% hydrochloric acid, 54.4 g of an aqueous saturated sodium bicarbonate solution, and 54.4 g of water, respectively, and concentrated with an evaporator to obtain 12.0 g of 2-(2-methoxymethyl-phenyl)-N-methyl-2-oxo-acetamide.

$^1$H-NMR (300 MHz, CDCl$_3$): δ ppm: 2.95 (d, J=5.14 Hz, 3H), 3.28 (s, 3H), 4.66 (s, 2H), 7.04 (s, 1H), 7.36-7.72 (m, 4H)

(3) Asymmetric reduction of 2-(2-methoxymethyl-phenyl)-N-methyl-2-oxo-acetamide Using Invented Transformant A reaction was performed according to the same manner as in Example 5 except that 2-(2-methoxymethyl-phenyl)-N-methyl-2-oxo-acetamide was used as a substrate. As a result, oily 2-(2-methoxymethyl-phenyl)-N-methyl-2-hydroxy-acetamide was obtained. Content analysis by liquid chromatography under the following condition showed that the conversion rate was 99.3%.

$^1$H-NMR analysis result of the resulting 2-(2-methoxymethyl-phenyl)-N-methyl-2-hydroxy-acetamide is shown below.

$^1$H-NMR (300 MHz, CDCl$_3$) σ 2.77 (d, J=4.85 Hz, 3H), 3.47 (S, 3H), 4.38 (d, J=10.6 Hz, 1H), 4.73 (d, J=10.6 Hz, 1H), 4-81 (S, 1H), 5.23 (S, 1H), 7.16 (S, 1H), 7.26-7.43 (m, 4H)

(Content Analysis Condition)
Column: SUMICHIRAL ODS A-212
Mobile phase: A solution 0.1% aqueous trifluoroacetic acid solution, B solution acetonitrile solution containing 0.1% trifluoroacetic acid

| Time(min) | A solution (%):B solution (%) |
|---|---|
| 0 | 80:20 |
| 20 | 10:90 |
| 30 | 1:99 |
| 30.1 | 80:2 |

Flow rate: 0.5 ml/min
Column temperature: 40° C.
Detection: 290 nm
Elusion time
2-(2-methoxymethyl-phenyl)-N-methyl-2-oxo-acetamide: 9.2 minutes To the resulting 2-(2-methoxymethyl-phenyl)-N-methyl-2-hydroxyacetamide was added hexane containing 10% 2-propanol, this was subjected to optical purity analysis by liquid chromatography under the following condition, and the optical purity was found to be 100% e.e. (elution time: 20.5 minutes).

Racemic 2-(2-methoxymethyl-phenyl)-N-methyl-2-hydroxyacetamide was synthesized by reducing 2-(2-methoxymethyl-phenyl)-N-methyl-2-oxo-acetamide with NaBH$_4$ in methanol.

(Optical Isomer Analysis Condition)
Column: CHIRALPAK OD-H (manufactured by Daicel Chemical Industries)
Mobile phase: hexane/2-propanol=90/10
Flow rate: 0.5 ml/min
Column temperature: 40° C.
Detection: 230 nm
Elusion time
  2-(2-methoxymethyl-phenyl)-N-methyl-2-oxo-acetamide: 18.5 minutes
  2-(2-methoxymethyl-phenyl)-N-methyl-2-hydroxyacetamide: 20.5 minutes, 21.3 minutes Example 9

Example of Reducing Reaction by Invented Transformant (7)

A reaction was performed according to the same manner as in Example 6 except that ethyl 2-(2-methoxymethyl-phenyl)-2-oxoacetate was used as a substrate.

As a result, oily ethyl 2-(2-methoxymethyl-phenyl)-2-hydroxy-acetate was obtained. Content analysis by liquid chromatography under the following condition showed that the conversion rate was 100%, $^1$H-NMR analysis result of the resulting ethyl 2-(2-methoxymethyl-phenyl)-2-hydroxy-acetate is shown below.

$^1$H-NMR (300 MHz, CDCl$_3$) σ 1.21 (t, J 7.09 Hz, 3H), 3.39 (S, 3H), 4.16-4.26 (m, 2H), 4.59 (d, J=636 Hz, 2H), 5.39 (S, 1H) 7.31-7.37 (m, 4H)

(Content Analysis Condition)
Column: SUMICHIRAL ODS A-212
Mobile phase: A solution 0.1% aqueous trifluoroacetic acid solution, B solution acetonitrile solution containing 0.1% trifluoroacetic acid

| Time (min) | A solution (%):B solution (%) |
|---|---|
| 0 | 80:20 |
| 20 | 10:90 |
| 30 | 1:99 |
| 30.1 | 80:20 |

Flow rate: 0.5 ml/min
Column temperature: 40° C.
Detection: 290 nm
Elusion time
ethyl 2-(2-methoxymethyl-phenyl)-2-oxoacetamide: 15.4 minutes To the resulting ethyl 2-(2-methoxymethyl-phenyl)-2-hydroxy-acetate was added hexane containing 10% 2-propanol, this was subjected to optical purity analysis by liquid chromatography under the condition, and the optical purity was found to be 100% e.e. (elution time: 13.6 minutes).

Racemic ethyl 2-(2-methoxymethyl-phenyl)-2-hydroxy-acetate was synthesized by reducing ethyl 2-(2-methoxymethyl-phenyl)-2-oxoacetate with NaBH$_4$ in methanol.

(Optical Isomer Analysis Condition)
Column: CHIRALPAK OD-H (manufactured by Daicel Chemical Industries)
Mobile phase: hexane/2-propanol=90/10
Flow rate: 0.5 ml/min
Column temperature: 40° C.
Detection: 230 nm
Elusion time
ethyl 2-(2-methoxymethyl-phenyl)-2-oxoacetate: 9.6 minutes
ethyl 2-(2-methoxymethyl-phenyl)-2-hydroxy-acetate: 13.2 minutes, 14.0 minutes Reference Example 2

Preparation of Invented Protein

Using the plasmid pTrcRxc, *E. coli* HB101 is transformed. The resulting transformant is inoculated in a sterilized LB medium (100 ml) containing 0.2 mM of IPTG and 50 μg/ml of ampicillin, and is shaking-cultured (30° C., 24 hours). The resulting culture is centrifuged to obtain about 0.6 g of wet bacterial cells. The wet bacterial cells are suspended in 10 ml of 20 mM potassium phosphate buffer (pH 7.0), and grind with a multibeads shocker (manufactured by Yasui Kikai, glass beads 0.1 mmΦ, 2500 rpm, 20 minutes) and a supernatant is filtered with a filter (0.45 μm) to obtain about 8 ml of the supernatant.

About 8 ml of the resulting supernatant is applied on an affinity interaction chromatography column [HiTrap BlueHP (manufactured by Amersham Pharmacia Biotech)][equilibrated with a 20 mM potassium phosphate buffer (pH 7.0)], and the column is eluted using, as a mobile phase, a potassium phosphate buffer with sodium chloride dissolved therein (concentration gradient of sodium chloride concentration 0-1.0 M) to obtain 2 ml of a fraction at a sodium chloride concentration of 0.5 to 0.8 M as a fraction having reductase activity.

The eluted fraction is concentrated using Amicon Ultra-4 (manufactured by MILLIPORE), and the buffer is exchanged with a mM Tris-HCL buffer (pH 7.5). This is applied on an ion exchange chromatography column [HiTrap DEAE Sepharose FF (manufactured by Amersham Pharmacia Biotech)] [equilibrated with a Tris-HCl buffer solution (20 mM, pH 7.5)], and the column is eluted using, as a mobile phase, a Tris-HCl buffer solution with sodium chloride dissolved therein (concentration gradient of sodium chloride concentration 0-0.5 M) to obtain 2 ml of an active fraction at a sodium chloride concentration of 0.1 to 0.2 M as a fraction having reductase activity.

The eluted fraction is concentrated using Amicon Ultra-4 (manufactured by MILLIPORE), and the buffer is exchanged with a 50 mM sodium phosphate buffer (pH 7.0) containing 0.15 M sodium chloride. The concentrated solution is passed through a gel filtration column [Superdex200 10/300GL (manufactured by Amersham Pharmacia Biotech)][mobile phase: 50 mM sodium phosphate buffer (pH 7.0) containing 0.15 M sodium chloride] to obtain 1 ml of an eluted fraction at a molecular weight of about 34000 dalton as a fraction having reductase activity.

Regarding the fraction obtained by the chromatography and so on, reductase activity is measured by the following procedure.

Three (3) mg of 2-(2-(2,5-dimethylphenoxymethyl)phenyl)-N-methyl-2-oxo-acetamide, 0.2 ml of the eluted fraction obtained by chromatography and so on, 9 mg of NADPH, 0.15 ml of butyl acetate, and 1.5 ml of a 100 mM phosphate buffer (pH 7.0) are mixed, and the mixture is stirred at 30° C. for 18 hours. Thereafter, 2 ml of ethyl acetate is added to the reaction solution, and this is centrifuged to obtain an organic layer. The organic layer is subjected to content analysis measurement by liquid chromatography under the following condition.

The reductase activity is determined from the residual amount of 2-(2-(2,5-dimethylphenoxymethyl)phenyl)-N-methyl-2-oxo-acetamide, and the production amount of (R)-2-(2-(2,5-dimethylphenoxymethyl)phenyl)-N-methyl-2-hydroxy-acetamide.

(Content Analysis Condition)
Column: SUMICHIRAL ODS A-212
Mobile phase: A solution 0.1% aqueous trifluoroacetic acid solution, B solution acetonitrile solution containing 0.1% trifluoroacetic acid

| Time (min) | A solution (%):B solution (%) |
|---|---|
| 0 | 80:20 |
| 20 | 10:90 |
| 30 | 1:99 |
| 30.1 | 80:20 |

Flow rate: 0.5 ml/min
Column temperature: 40° C.
Detection: 290 nm

INDUSTRIAL APPLICABILITY

According to the present invention, optically-active mandelic acid compounds can be efficiently obtained by reducing phenylglyoxylic acid compounds.

The invention claimed is:

1. An isolated DNA comprising any of the following nucleotide sequence:
   a) a nucleotide sequence encoding the amino acid sequence of SEQ ID NO:1;
   b) the nucleotide sequence of SEQ ID NO:2; and
   c) a nucleotide sequence encoding an amino acid sequence in which one amino acid is deleted, substituted or added in the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically-active ortho-substituted mandelic acid compound.

2. An isolated DNA in which a promoter functional in a host cell and a DNA comprising any nucleotide sequence of the following a) to c) are operably linked:
   a) a nucleotide sequence encoding the amino acid sequence of SEQ ID NO:1;
   b) a nucleotide sequence encoding an amino acid sequence in which one amino acid is deleted, substituted or added in the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically active ortho-substituted mandelic acid compound; and
   c) the nucleotide sequence of SEQ ID NO:2.

3. A recombinant vector comprising a DNA comprising any of the following nucleotide sequence:
   a) a nucleotide sequence encoding the amino acid sequence of SEQ ID NO:1;
   b) the nucleotide sequence of SEQ ID NO:2; and
   c) a nucleotide sequence of a DNA, wherein the DNA has at least 99% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically-active ortho-substituted mandelic acid compound.

4. A process for producing a transformant comprising a step of introducing the recombinant vector of claim 3 into a host cell.

5. A transformant transformed with a DNA operatively linked to a promoter functional in a host cell, wherein said DNA comprising any nucleotide sequence of the following a) to c):
   a) a nucleotide sequence encoding the amino acid sequence of SEQ ID NO:1;
   b) a nucleotide sequence of a DNA, wherein the DNA has at least 99% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically-active ortho-substituted mandelic acid compound; and
   c) the nucleotide sequence of SEQ ID NO:2.

6. The transformant according to claim 5, which is a microorganism.

7. The transformant according to claim 5, which is *Escherichia coli*.

8. A transformant transformed with a DNA comprising any of the following nucleotide sequence:
   a) a nucleotide sequence encoding the amino acid sequence of SEQ ID NO:1;
   b) a nucleotide sequence of a DNA, wherein the DNA has at least 99% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically-active ortho-substituted mandelic acid compound; and
   c) the nucleotide sequence of SEQ ID NO:2.

9. A process for producing an optically-active alcohol compound comprising reacting the transformant of claim 8 with a prochiral carbonyl compound.

10. The process according to claim 9, wherein the prochiral carbonyl compound is an ortho-substituted phenylglyoxalic acid compound represented by the formula (1):

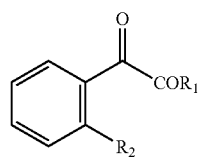

wherein R₁ represents an optionally substituted amino group, or an optionally substituted alkoxy group, and R₂ represents an optionally substituted C1-8 alkyl group and the optically-active alcohol compound is an optically-active ortho-substituted mandelic acid compound represented by the formula (2):

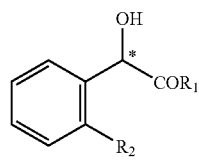

wherein R₁ and R₂ are as defined above, and a carbon atom with a * symbol is an asymmetric carbon, atom.

11. A recombinant vector comprising i) a DNA comprising any nucleotide sequence of the following a) to c) and ii) a DNA comprising a nucleotide sequence encoding an amino acid sequence of a protein having the ability to convert oxidized β-nicotinamide adenine dinucleotide or oxidized β-nicotinamide adenine dinucleotide phosphate into a reduced form:
   a) a nucleotide sequence encoding the amino acid sequence of SEQ ID NO:1;
   b) a nucleotide sequence of a DNA, wherein the DNA has at least 99% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically-active ortho-substituted mandelic acid compound; and
   c) the nucleotide sequence of SEQ ID NO:2.

12. The recombinant vector according to claim 11, wherein the protein having the ability to convert oxidized β-nicotinamide adenine dinucleotide or oxidized β-nicotinamide adenine dinucleotide phosphate into a reduced form is glucose dehydrogenase.

13. The recombinant vector according to claim 12, wherein the protein having glucose dehydrogenase activity is glucose dehydrogenase derived from *Bacillus megaterium*.

14. A transformant transformed with the recombinant vector of claim 11.

15. The transformant according to claim 14, which is a microorganism.

16. The transformant according to claim 14, which is *Escherichia coli*.

17. A transformant transformed with a DNA comprising any nucleotide sequence of the following a) to c) and a DNA comprising a nucleotide sequence encoding an amino acid sequence of a protein having the ability to convert oxidized β-nicotinamide adenine dinucleotide or oxidized β-nicotinamide adenine dinucleotide phosphate into a reduced form:
   a) a nucleotide sequence encoding the amino acid sequence of SEQ ID NO:1;
   b) a nucleotide sequence of a DNA, wherein the DNA has at least 99% sequence homology with a DNA comprising a nucleotide sequence encoding the amino acid sequence of SEQ ID NO:1, and wherein the nucleotide sequence encodes an amino acid sequence of a protein having the ability to asymmetrically reduce an ortho-substituted phenylglyoxalic acid to produce corresponding optically active ortho-substituted mandelic acid compound; and
   c) the nucleotide sequence of SEQ ID NO:2.

18. A process for producing an optically-active alcohol compound comprising reacting the transformant of claim 17 with a prochiral carbonyl compound.

19. The process according to claim 18, wherein the prochiral carbonyl compound is an ortho-substituted phenylglyoxalic acid compound represented by the formula (1):

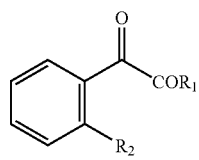

wherein R₁ represents an optionally substituted amino group, or an optionally substituted alkoxy group, and R₂ represents an optionally substituted C1-8 alkyl group and the optically-active alcohol compound is an optically-active ortho-substituted mandelic acid compound represented by the formula (2):

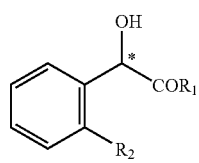

wherein R₁ and R₂ are as defined above, and a carbon atom with a * symbol is an asymmetric carbon atom.

* * * * *